(12) United States Patent
Berry et al.

(10) Patent No.: US 8,998,920 B2
(45) Date of Patent: *Apr. 7, 2015

(54) INSERTION TOOL FOR INTER-BODY VERTEBRAL PROSTHETIC DEVICE WITH SELF-DEPLOYING SCREWS

(71) Applicant: Amicus Design Group, LLC, Grand Prairie, TX (US)

(72) Inventors: Bret M. Berry, Tallahassee, FL (US); Richard D. Guyer, Plano, TX (US); Jack Zigler, Plano, TX (US); Adam A. Pike, Bountiful, UT (US); Randall F. Lee, Grand Prairie, TX (US)

(73) Assignee: Amicus Design Group, LLC, Grand Prairie, TX (US)

( * ) Notice: Subject to any disclaimer, the term of this patent is extended or adjusted under 35 U.S.C. 154(b) by 27 days.

This patent is subject to a terminal disclaimer.

(21) Appl. No.: 13/752,923

(22) Filed: Jan. 29, 2013

(65) Prior Publication Data

US 2014/0058514 A1 Feb. 27, 2014

Related U.S. Application Data

(63) Continuation of application No. 12/553,740, filed on Sep. 3, 2009, now Pat. No. 8,425,528, which is a continuation-in-part of application No. 12/339,766, filed on Dec. 19, 2008.

(51) Int. Cl.
*A61B 17/58* (2006.01)
*A61B 17/60* (2006.01)
(Continued)

(52) U.S. Cl.
CPC .............. *A61F 2/4611* (2013.01); *A61B 17/86* (2013.01); *A61F 2/4465* (2013.01); *A61F 2/447* (2013.01);
(Continued)

(58) Field of Classification Search
USPC ................. 606/86 A, 86 B, 99, 914, 915; 623/17.16; 81/57.14, 57.3, 453–455
See application file for complete search history.

(56) References Cited

U.S. PATENT DOCUMENTS

| 4,863,476 A | 9/1989 | Shepperd |
| 5,387,218 A | 2/1995 | Meswania |

(Continued)

FOREIGN PATENT DOCUMENTS

| WO | 2004078218 A2 | 9/2004 |
| WO | 2010121028 A2 | 10/2010 |

OTHER PUBLICATIONS

International Search Report and Written Opinion for corresponding PCT application No. PCT/US2013/026689, May 8, 2013.
(Continued)

*Primary Examiner* — Andrew Yang
*Assistant Examiner* — Diana S Jones
(74) *Attorney, Agent, or Firm* — Matthew B. Dernier, Esq.; Gibson & Dernier LLP

(57) ABSTRACT

An apparatus for inserting an intervertebral prosthesis within a spine of a mammal includes: a handle including a drive nut operating to produce rotational torque in response to user-input about a central axis; a first drive shaft including a proximal end in communication with the drive nut, receiving rotational torque therefrom, and imparting rotational torque to the first drive shaft about a first axis, which is laterally offset from the central axis; and a distal end of the first drive shaft including a first drive head; and a chuck disposed at a distal end of the tool for engaging the intervertebral prosthesis during implantation, wherein the first drive shaft extends through the chuck and the first drive head engages a first gear of the intervertebral prosthesis, such that rotation of the first gear causes rotation and deployment of a first anchoring element of the intervertebral prosthesis.

11 Claims, 13 Drawing Sheets

(51) Int. Cl.
    *A61F 2/00*     (2006.01)
    *A61F 2/44*     (2006.01)
    *A61F 2/46*     (2006.01)
    *A61B 17/86*    (2006.01)
    *A61F 2/28*     (2006.01)
    *A61F 2/30*     (2006.01)

(52) U.S. Cl.
    CPC . *A61F 2002/2817* (2013.01); *A61F 2002/2835* (2013.01); *A61F 2002/30281* (2013.01); *A61F 2002/30523* (2013.01); *A61F 2002/30525* (2013.01); *A61F 2002/30579* (2013.01); *A61F 2002/30787* (2013.01); *A61F 2002/30841* (2013.01); *A61F 2002/30904* (2013.01); *A61F 2002/4475* (2013.01); *A61F 2002/4627* (2013.01); *A61F 2002/4629* (2013.01); *A61F 2220/0025* (2013.01); *A61F 2230/0086* (2013.01); *A61F 2310/00023* (2013.01); *A61F 2310/00179* (2013.01)

(56) References Cited

U.S. PATENT DOCUMENTS

| | | |
|---|---|---|
| 5,522,899 A | 6/1996 | Michelson |
| 5,609,635 A | 3/1997 | Michelson |
| 5,658,335 A | 8/1997 | Allen |
| 5,800,547 A | 9/1998 | Schaefer |
| 5,800,550 A | 9/1998 | Sertich |
| 6,022,363 A | 2/2000 | Walker et al. |
| 6,066,175 A | 5/2000 | Henderson et al. |
| 6,113,638 A | 9/2000 | Williams et al. |
| 6,190,414 B1 | 2/2001 | Young et al. |
| 6,306,170 B2 | 10/2001 | Ray |
| 6,461,359 B1 | 10/2002 | Tribus et al. |
| 6,527,803 B1 | 3/2003 | Crozet |
| 6,572,619 B2 | 6/2003 | Santilli |
| 6,749,636 B2 | 6/2004 | Michelson |
| 6,752,832 B2 | 6/2004 | Neumann |
| 6,770,096 B2 | 8/2004 | Bolger et al. |
| 6,800,092 B1 | 10/2004 | Williams et al. |
| 6,805,714 B2 | 10/2004 | Sutcliffe |
| 6,834,567 B2 * | 12/2004 | Rosetto ................ 81/57.22 |
| 6,899,735 B2 | 5/2005 | Coates et al. |
| 7,018,415 B1 | 3/2006 | McKay |
| 8,062,374 B2 | 11/2011 | Markworth |
| 8,343,219 B2 | 1/2013 | Allain |
| 2002/0049444 A1 | 4/2002 | Knox |
| 2002/0143399 A1 | 10/2002 | Sutcliffe |
| 2003/0014113 A1 | 1/2003 | Ralph et al. |
| 2003/0014114 A1 | 1/2003 | Ralph et al. |
| 2003/0014115 A1 | 1/2003 | Ralph et al. |
| 2003/0014116 A1 | 1/2003 | Ralph et al. |
| 2003/0023309 A1 | 1/2003 | Ralph et al. |
| 2003/0023310 A1 | 1/2003 | Ralph et al. |
| 2003/0025408 A1 | 2/2003 | Miekka et al. |
| 2003/0028252 A1 | 2/2003 | Ralph et al. |
| 2003/0073998 A1 | 4/2003 | Pagliuca et al. |
| 2003/0074075 A1 | 4/2003 | Thomas, Jr. et al. |
| 2003/0125739 A1 | 7/2003 | Bagga et al. |
| 2003/0187436 A1 | 10/2003 | Bolger |
| 2003/0233147 A1 | 12/2003 | Nicholson |
| 2004/0002764 A1 | 1/2004 | Gainor et al. |
| 2004/0020568 A1 | 2/2004 | Phelps et al. |
| 2004/0024463 A1 | 2/2004 | Thomas, Jr. et al. |
| 2004/0039384 A1 | 2/2004 | Boehm, Jr. et al. |
| 2004/0093089 A1 | 5/2004 | Ralph et al. |
| 2004/0097924 A1 | 5/2004 | Lambrecht et al. |
| 2004/0133201 A1 | 7/2004 | Shluzas et al. |
| 2004/0153075 A1 | 8/2004 | Roger |
| 2004/0158326 A1 | 8/2004 | Ralph et al. |
| 2004/0176853 A1 | 9/2004 | Sennett et al. |
| 2004/0199254 A1 | 10/2004 | Louis |
| 2005/0013832 A1 | 1/2005 | Rose |
| 2005/0013833 A1 | 1/2005 | Simonnet |
| 2005/0021030 A1 | 1/2005 | Pagliuca et al. |
| 2005/0033297 A1 | 2/2005 | Davison |
| 2005/0033299 A1 | 2/2005 | Shluzas |
| 2005/0043798 A1 | 2/2005 | Eckman |
| 2005/0049590 A1 | 3/2005 | Alleyne |
| 2005/0090822 A1 | 4/2005 | DiPoto |
| 2005/0131543 A1 | 6/2005 | Benzel et al. |
| 2005/0159819 A1 | 7/2005 | McCormack et al. |
| 2005/0261684 A1 | 11/2005 | Shaolian et al. |
| 2005/0273173 A1 | 12/2005 | Gordon et al. |
| 2005/0273174 A1 | 12/2005 | Gordon et al. |
| 2005/0273175 A1 | 12/2005 | Gordon et al. |
| 2005/0283246 A1 | 12/2005 | Cauthen et al. |
| 2005/0283247 A1 | 12/2005 | Gordon et al. |
| 2005/0283248 A1 | 12/2005 | Gordon et al. |
| 2006/0024162 A1 | 2/2006 | Giffin |
| 2006/0047342 A1 | 3/2006 | Khoshnevis |
| 2006/0058800 A1 | 3/2006 | Ainsworth et al. |
| 2006/0079898 A1 | 4/2006 | Ainsworth et al. |
| 2006/0095136 A1 | 5/2006 | McLuen |
| 2006/0142859 A1 | 6/2006 | McLuen |
| 2006/0155379 A1 | 7/2006 | Heneveld, Sr. et al. |
| 2006/0195092 A1 | 8/2006 | Barry |
| 2006/0200239 A1 | 9/2006 | Rothman et al. |
| 2006/0229729 A1 | 10/2006 | Gordon et al. |
| 2006/0235391 A1 | 10/2006 | Sutterlin, III |
| 2006/0241621 A1 | 10/2006 | Moskowitz et al. |
| 2006/0247643 A1 | 11/2006 | Bhatnagar et al. |
| 2006/0247644 A1 | 11/2006 | Bhatnagar et al. |
| 2006/0247784 A1 | 11/2006 | Kim |
| 2006/0253132 A1 | 11/2006 | Evans et al. |
| 2006/0253201 A1 | 11/2006 | McLuen |
| 2006/0276790 A1 | 12/2006 | Dawson et al. |
| 2006/0276897 A1 | 12/2006 | Winslow |
| 2006/0287731 A1 | 12/2006 | Cauthen, III et al. |
| 2007/0005140 A1 | 1/2007 | Kim et al. |
| 2007/0010816 A1 | 1/2007 | Wilkinson et al. |
| 2007/0010821 A1 | 1/2007 | Wilkinson et al. |
| 2007/0021750 A1 | 1/2007 | Shluzas et al. |
| 2007/0038222 A1 | 2/2007 | Bhatnagar et al. |
| 2007/0043361 A1 | 2/2007 | Malandain et al. |
| 2007/0043362 A1 | 2/2007 | Malandain et al. |
| 2007/0043363 A1 | 2/2007 | Malandain et al. |
| 2007/0049943 A1 | 3/2007 | Moskowitz et al. |
| 2007/0049944 A1 | 3/2007 | Stone et al. |
| 2007/0055379 A1 | 3/2007 | Stone et al. |
| 2007/0078460 A1 | 4/2007 | Frigg et al. |
| 2007/0093827 A1 | 4/2007 | Warnick |
| 2007/0100348 A1 | 5/2007 | Cauthen, III et al. |
| 2007/0112351 A1 | 5/2007 | Assell et al. |
| 2007/0156245 A1 | 7/2007 | Cauthen, III et al. |
| 2007/0162129 A1 | 7/2007 | Edie et al. |
| 2007/0162139 A1 | 7/2007 | Ralph et al. |
| 2007/0168043 A1 | 7/2007 | Ferree |
| 2007/0179623 A1 | 8/2007 | Trieu et al. |
| 2007/0198021 A1 | 8/2007 | Wales |
| 2007/0219634 A1 | 9/2007 | Greenhalgh et al. |
| 2007/0233083 A1 | 10/2007 | Abdou |
| 2007/0239159 A1 | 10/2007 | Altarac et al. |
| 2007/0239160 A1 | 10/2007 | Zipnick et al. |
| 2007/0260245 A1 | 11/2007 | Malandain et al. |
| 2007/0265623 A1 | 11/2007 | Malandain et al. |
| 2007/0270842 A1 | 11/2007 | Bankoski et al. |
| 2007/0270960 A1 | 11/2007 | Bonin, Jr. et al. |
| 2007/0276370 A1 | 11/2007 | Altarac et al. |
| 2007/0276372 A1 | 11/2007 | Malandain et al. |
| 2007/0276373 A1 | 11/2007 | Malandain |
| 2007/0293948 A1 | 12/2007 | Bagga et al. |
| 2008/0009826 A1 | 1/2008 | Miller et al. |
| 2008/0009828 A1 | 1/2008 | Miller et al. |
| 2008/0009880 A1 | 1/2008 | Warnick et al. |
| 2008/0009944 A1 | 1/2008 | McGuckin, Jr. |
| 2008/0018660 A1 | 1/2008 | Nenonen et al. |
| 2008/0021687 A1 | 1/2008 | Hunter et al. |
| 2008/0021692 A1 | 1/2008 | Chaudhry et al. |
| 2008/0027449 A1 | 1/2008 | Gundlapalli et al. |
| 2008/0027550 A1 | 1/2008 | Link et al. |
| 2008/0033558 A1 | 2/2008 | Zucherman et al. |
| 2008/0033559 A1 | 2/2008 | Zucherman et al. |

(56) References Cited

U.S. PATENT DOCUMENTS

| | | |
|---|---|---|
| 2008/0033560 A1 | 2/2008 | Zucherman et al. |
| 2008/0039947 A1 | 2/2008 | Zucherman et al. |
| 2008/0046081 A1 | 2/2008 | Zucherman et al. |
| 2008/0051898 A1 | 2/2008 | Zucherman et al. |
| 2008/0051899 A1 | 2/2008 | Zucherman et al. |
| 2008/0058935 A1 | 3/2008 | Malandain et al. |
| 2008/0071274 A1 | 3/2008 | Ensign |
| 2008/0071376 A1 | 3/2008 | Kohm et al. |
| 2008/0077136 A1 | 3/2008 | Triplett et al. |
| 2008/0082170 A1 | 4/2008 | Peterman |
| 2008/0108990 A1 | 5/2008 | Mitchell et al. |
| 2008/0109005 A1 | 5/2008 | Trudeau et al. |
| 2008/0114454 A1 | 5/2008 | Peterman et al. |
| 2008/0119935 A1 | 5/2008 | Alvarez |
| 2008/0140207 A1 | 6/2008 | Olmos et al. |
| 2008/0147192 A1 | 6/2008 | Edidin et al. |
| 2008/0147194 A1 | 6/2008 | Grotz et al. |
| 2008/0154382 A1 | 6/2008 | de Villiers et al. |
| 2008/0161933 A1 | 7/2008 | Grotz et al. |
| 2008/0167686 A1 | 7/2008 | Trieu et al. |
| 2008/0167718 A1 | 7/2008 | Protopsaltis |
| 2008/0177306 A1 | 7/2008 | Lamborne et al. |
| 2008/0221694 A1 | 9/2008 | Warnick et al. |
| 2008/0275455 A1 | 11/2008 | Berry et al. |
| 2008/0275456 A1 | 11/2008 | Vonwiller et al. |
| 2008/0281424 A1 | 11/2008 | Parry et al. |
| 2008/0288075 A1 | 11/2008 | Zucherman et al. |
| 2008/0292161 A1 | 11/2008 | Funk et al. |
| 2008/0294263 A1 | 11/2008 | Altarac et al. |
| 2009/0012528 A1 | 1/2009 | Aschmann et al. |
| 2009/0018660 A1 | 1/2009 | Roush |
| 2009/0030522 A1 | 1/2009 | Cauthen, III et al. |
| 2009/0036937 A1 | 2/2009 | Cauthen, III et al. |
| 2009/0036989 A1 | 2/2009 | Cauthen, III et al. |
| 2009/0036990 A1 | 2/2009 | Cauthen, III et al. |
| 2009/0043343 A1 | 2/2009 | Wales |
| 2009/0043394 A1 | 2/2009 | Zdeblick et al. |
| 2009/0054988 A1 | 2/2009 | Hess |
| 2009/0164020 A1 | 6/2009 | Janowski |
| 2010/0100100 A1* | 4/2010 | Refai et al. ............... 606/99 |
| 2010/0137989 A1 | 6/2010 | Armstrong |
| 2010/0185289 A1 | 7/2010 | Kirwan et al. |
| 2010/0262247 A1 | 10/2010 | Arnin |

OTHER PUBLICATIONS

International Preliminary Report on Patentability and Written Opinion for related application PCT/US2013/026689, dated Oct. 2, 2014.
Promotional material for SynFixTM (www.synthes.com).
Promotional material for VerteBridgeTM (www.ldrholding.com).
Promotional material for Stalif TM.
International Search Report and Written Opinion for corresponding PCT application No. PCT/US2009/060602, Jan. 11, 2010.
Office Action for related U.S. Appl. No. 12/533,740, dated Dec. 23, 2011.
Office Action for related U.S. Appl. No. 12/533,740, dated Jul. 2, 2012.
Office Action for corresponding U.S. Appl. No. 13/770,511, dated Sep. 20, 2013.

* cited by examiner

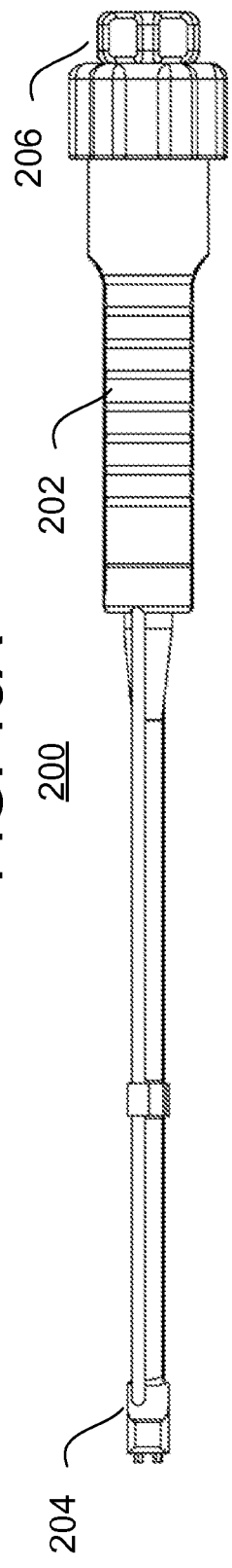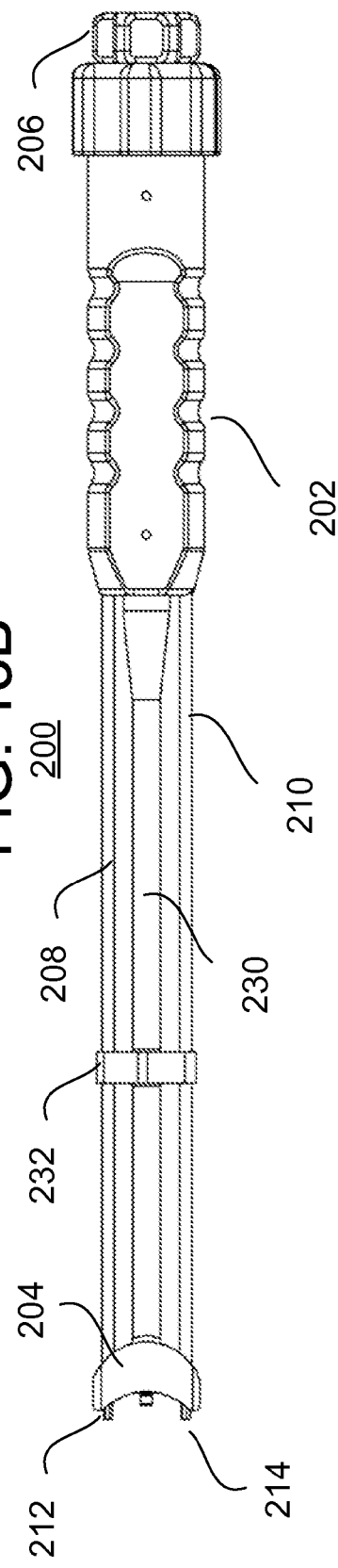

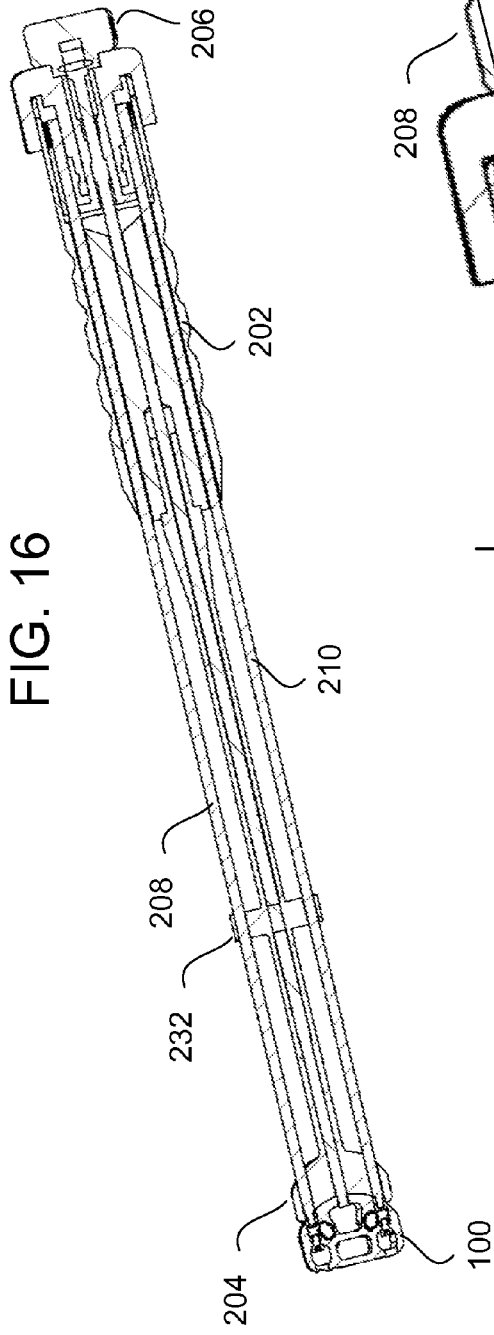
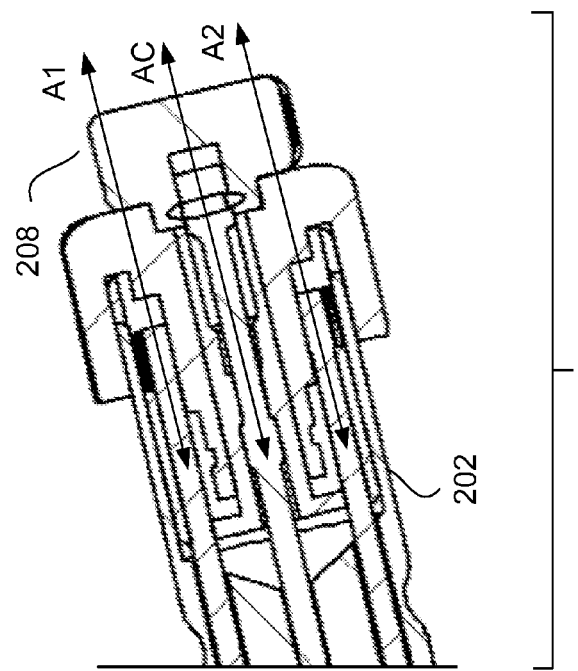
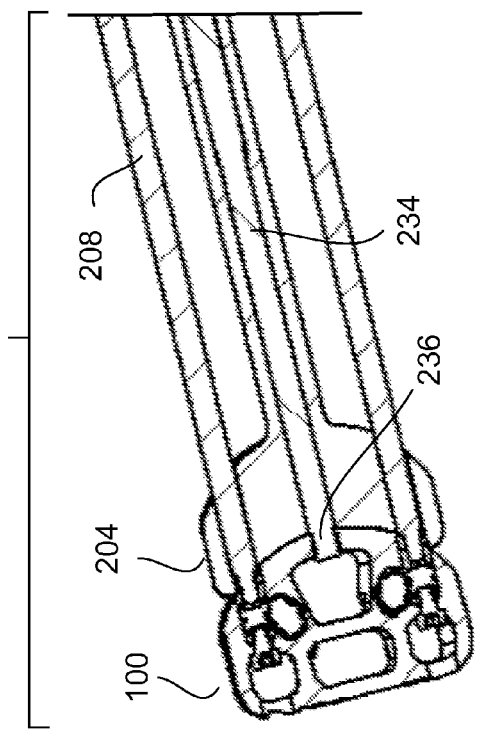

INSERTION TOOL FOR INTER-BODY VERTEBRAL PROSTHETIC DEVICE WITH SELF-DEPLOYING SCREWS

CROSS REFERENCE TO RELATED APPLICATIONS

This application is a Continuation application of U.S. patent application Ser. No. 12/553,740, filed Sep. 3, 2009, now allowed, which is a Continuation-In-Part of U.S. patent application No. Ser. No. 12/339,766, filed Dec. 19, 2008, now pending, the entire disclosures of which are hereby incorporated by reference.

BACKGROUND

The present disclosure generally relates to apparatus and methods for treatment of spinal disorders using an intervertebral prosthesis which is disposed in an intervertebral space (or cavity) following removal of a damaged or diseased intervertebral disc.

The bones and connective tissue of an adult human spinal column consists of more than twenty discrete bones coupled sequentially to one another by a tri-joint complex. Each tri-joint complex includes an anterior disc and two posterior facet joints. The anterior space between adjacent bones are cushioned by cartilage spacers referred to as intervertebral discs. These more than twenty bones are anatomically categorized as being members of one of four classifications: cervical, thoracic, lumbar, or sacral. The cervical portion of the spine, which comprises the top of the spine, up to the base of the skull, includes the first seven vertebrae. The intermediate twelve bones are the thoracic vertebrae, and connect to the lower spine comprising the five lumbar vertebrae. The base of the spine includes the sacral bones (including the coccyx). The component bones of the cervical spine are generally smaller than those of the thoracic spine, which are in turn smaller than those of the lumbar region. The sacral region connects laterally to the pelvis.

The spinal column is highly complex in that it includes these more than twenty bones coupled to one another, housing and protecting critical elements of the nervous system having innumerable peripheral nerves and circulatory bodies in close proximity. In spite of these conditions, the spine is a highly flexible structure, capable of a high degree of curvature and twist in nearly every direction.

Genetic or developmental irregularities, trauma, chronic stress, tumors, and degenerative wear are a few of the factors that can result in spinal pathologies for which surgical intervention may be necessary. A variety of systems have been disclosed in the art that achieve immobilization and/or fusion of adjacent bones by implanting artificial assemblies in or on the spinal column. The region of the back that needs to be immobilized, as well as the individual variations in anatomy, determines the appropriate surgical protocol and implantation assembly. The spine surgical community has accepted intervertebral devices (commonly known as interbody spacers, and allograft transplants) as part of the state of the art and routine practice employs such devices in the reconstruction of collapsed inter-vertebral disc spaces.

Surgeons insert these intervertebral devices to facilitate bone fusion in between and into the contiguous involved vertebrae. This fusion creates a new solid bone mass, which acts to hold the spinal segment at an appropriate biomechanically restored height as well as to stop motion in a segment of the spine in which the patient is experiencing pain. Items surgically placed in these involved interbody regions can thus stimulate interbody bone in-growth such that the operated anterior spinal segments heal into a contiguous bone mass; in other words, a fusion occurs. Further, the surgical community uses such man-made implants or biological options to provide weight bearing support between adjacent vertebral bodies, and thereby correct or alleviate a variety of clinical problems. In this regard, surgeons use intervertebral spinal implants/transplants for surgical therapy for degenerative disc disease (DDD), discogenic low back pain, spondylolisthesis, reconstruction following tumor or infection surgery, and other spine related maladies requiring surgical intervention.

In many implant designs, a relatively hard or sturdy implant construct is formed from a selected biocompatible material such as metal, ceramic, or carbon fiber-reinforced polymer. This implant construct often has a partially open or porous configuration and is coated or partially filled with a selected bone ingrowth-enhancing substance, such as harvested bone graft supplied from the patient, human donor allograft bone transplant material supplied by a tissue bank, genetically cultivated bone growing protein substitutes, and/or other biological/biochemical bone extenders. Such devices, when implanted into the intervertebral space, promote ingrowth of blood supply and grow active and live bone from the adjacent spinal vertebrae to inter-knit with the implant, thereby eventually immobilizing or fusing the adjacent spinal vertebrae. Such implants also commonly include a patterned exterior surface such as a ribbed or serrated surface, or screw thread geometry, to achieve enhanced mechanical locking with the adjacent vertebrae during the bone ingrowth/fusion process.

With respect to the failure of the intervertebral disc, the interbody fusion cage has generated substantial interest because it can be implanted laparoscopically into the anterior of the spine, thus reducing operating room time, patient recovery time, and scarification. Conventional intervertebral body cages generally comprise a tubular metal body having an external surface threading. They are inserted transverse to the axis of the spine, into preformed cylindrical holes at the junction of adjacent vertebral bodies. The cages include holes through which the adjacent bones are to grow. Additional materials, for example autogenous bone graft materials, may be inserted into the hollow interior of the cage to incite or accelerate the growth of the bone into the cage.

There are several commercially available devices that operate as stand-alone (that is, without support from an additional construct such as an anterior plate and screws, or posteriorly placed screws and/or rods placed into the pedicles or facet joints) interbody fusion devices. These devices include the Stalif™, SynFix™, and the VerteBridge™. The Stalif™ is a device for the fusion of the lumbar spine. The implant is inserted and fixed via diverging screws passing through pre-drilled apertures of the device that penetrate into the vertebral bodies. The screws are manually placed into the apertures of the device and are driven using an appropriate tool, such as a surgical screw driver. The Stalif™ is available from Surgicraft Limited Corporation, 16 The Oaks Clews Road Redditch, United Kingdom (www.surgicraft.co.uk). The SynFix™ is also a device that is placed in an intervertebral space and fixed via diverging screws passing through the device and into the vertebral bodies. Again, the screws are manually placed into the apertures of the device and are driven using a surgical screw driver. The SynFix™ is available from Synthes, Inc., 1302 Wrights Lane East, West Chester, Pa. 19380 (www.synthes.com). The VerteBridge™ is a device for the fusion of the spine in which anchoring blades are press-driven (using a specialized tool) through apertures in the device and into the respective vertebral bodies to fix the device in place. The VerteBridge™ is available through the LDR Spine (www.ldrholding.com).

All of the above-described devices have an anchor which is secondarily added to the initial device. The Stalif™ and SynFix™ devices employ screws while the VerteBridge™ utilizes a blade anchor. Both the Stalif™ and SynFix™ devices require the screws to be inserted at trajectories that are difficult to achieve given common human anatomical structures, especially at the spinal level L5-S1. Additionally, the proximal end of the screws may protrude anteriorly, causing potential irritation to the great vessels. The VerteBridge™ has a pair of blades inserted after the initial device is put in place. The blades are supposed to flex enough to curve within the device, and to exhibit sufficient strength to cut through bone. These blades, although flexible, need to be able to hold the vertebral bodies in place. In practice, these features are not always achieved.

A number of devices have been developed, which employ self-contained anchoring elements that are deployed after the device is placed into the intervertebral space. For example, U.S. Patent Application Pub. No. 2006/0241621 (incorporated herein in its entirety) discloses a device for joining intervertebral members together using a self-drilling screw apparatus. The screw apparatus includes a shell and first and second screw members having tapered ends and threaded bodies that are disposed within the shell. A drive mechanism rotatably drives the first and second screw members from the shell in precisely co-axial, opposite directions, which causes the screw members to embed themselves in the vertebral bodies. U.S. Pat. No. 5,800,550 (incorporated herein in its entirety) discloses a device for joining intervertebral members together using a self-deploying pair of posts. The apparatus includes a body and first and second post members that are disposed within the body. A drive mechanism press-drives the first and second posts from the body in precisely co-axial, opposite directions (longitudinally aligned with the spine), which causes the posts to embed themselves in the vertebral bodies. The problems with these devices include that the co-axial, opposite deployment of the screws/posts is not an ideal configuration for fixing an intervertebral device. Indeed, such a deployment may permit slippage of the device during or after deployment because of the natural stresses applied to the device from the patient's anatomical spinal structures.

Given the disadvantageous features of the prior art devices, there is a need for a new intervertebral device that includes self-contained anchoring members that deploy in desirable transverse directions, as well as instrumentation for inserting the device in a patient's spine.

SUMMARY OF THE INVENTION

Embodiments of the present invention are stand-alone interbody devices, which may be designed in the general style of an anterior lumbar interbody fusion (ALIF) device, a transforaminal lumbar interbody fusion (TLIF) device, a posterior lumbar interbody fusion (PLIF) device, an extreme lateral or direct lateral interbody device fusion device, or a cervical interbody device.

The device includes a body made from any variety of structural biomaterial including, but not limited to, polyetheretherketone (PEEK), Titanium, ceramic, etc. The body may have serrated superior and/or inferior surfaces to provide initial resistance against migration. Additionally, there may be at least one opening extending from the superior surface to the inferior surface for the purpose of containing osteo-inductive material, such as autograft, bone morphogenetic protein (BMP), bone marrow aspirate, etc.

The body contains at least one screw therein, which screw may be deployed from the body of the device via a gear drive in a transverse direction with respect to a normal axis of the device. In one or more embodiments, there may be one or more holes on an anterior face of the body for engagement with an inserter device. One or more of the holes may also serve as the openings for a gear drive engagement tool to operate the gear and deploy the at least one screw from the body.

The gear drive is disposed within the body of the device and includes teeth that mesh with, and interact with, the threads of the one or more screws such that turning the gear turns the screws, thereby deploying same from the body. Thus, the gear drives the one or more screws into the vertebral bodies, securing the device in place. The gear may be driven via a driver, preferably on an inserter for the device itself. After deployment of the one or more screws from the body into the vertebral bodies, the gear may be locked into place via a set screw (although any other known or hereinafter developed methods may also be used to secure the gear).

The screws of the device are initially hidden within the body. This allows for the device to be easily inserted within the disc space without the screws protruding. The screws must be self-drilling and self-tapping in order to cut into the vertebral body bone. Two or more screws may be driven by one gear, which may require different thread geometry than a single screw configuration, such as one screw having a left-handed thread, the other screw having a right-handed thread. The screw may have a larger diameter on the proximal end (the end remaining in the body of the device), such that the screw may engage the vertebral body at a specified point, yet restricting deployment of the screw from the device such that the screw is prevented from completely exiting the device.

One of the benefits of the embodiments of the invention is the ease with which the device may be used. There are fewer steps as compared with conventional devices because all of the screws can be deployed from the body of the device using the same tool from inserting the device into the intervertebral space. Furthermore, because the screws are self-contained, there is no difficult trajectory needed to place the screws as with previous devices. As opposed to devices employing blades or posts, the embodiments of the invention employ screws, which provide better fixation and stabilization. Because screws can be deployed in a variety of angles, they can provide better fixation.

In accordance with one or more embodiments of the present invention, an intervertebral prosthesis, includes: a body including first and second spaced apart major surfaces and at least anterior and posterior sidewalls extending therebetween, the first major surface for engaging an endplate of a first vertebral bone of a spine, and the second major surface for engaging an endplate of an adjacent, second vertebral bone of the spine, and the first and second major surfaces defining a longitudinal axis extending substantially normal to said surfaces; a first aperture extending from within the body, transversely with respect to the longitudinal axis, and opening at the first major surface; a first anchoring element disposed within the first aperture and including a threaded shaft having proximal and distal ends; and a first gear disposed adjacent to and in meshed, threaded communication with the threaded shaft of the first anchoring element such that rotation of the first gear causes rotation of the first anchoring element.

A driving rotational force on the first gear causes the first anchoring element to rotate, deploy from the body, and thread into the first vertebral bone in a direction transverse to the longitudinal axis of the body and the spine.

In accordance with one or more aspects of the present invention, an apparatus for inserting an intervertebral prosthesis within a spine of a mammal may include: a handle disposed at a proximal end of the tool and including a drive nut operating to produce rotational torque in response to user-input about a central axis; and a first drive shaft including proximal and distal ends; the proximal end in communication with the drive nut, receiving rotational torque therefrom, and imparting rotational torque to the first drive shaft about a first axis, which is laterally offset from the central axis; and the distal end of the first drive shaft including a first drive head. The first drive head may engage a first gear of the intervertebral prosthesis, such that rotation of the first gear causes rotation and deployment of a first anchoring element of the intervertebral prosthesis.

Additionally, the apparatus may further include a second drive shaft including proximal and distal ends, the proximal end being in communication with the drive nut, receiving rotational torque therefrom, and imparting rotational torque to the second drive shaft about a second axis. The second axis may be laterally offset from both the central axis and the first axis. The distal end of the second drive shaft includes a second drive head, wherein the second drive head operates to engage a second gear of the intervertebral prosthesis, such that rotation of the second gear causes rotation and deployment of a second anchoring element of the intervertebral prosthesis.

The apparatus may further include a main drive gear rotatable about a central axis, and coupled to, and receiving the rotational torque from, the drive nut. The first and/or second drive shaft may include a pickup gear in meshed communication with the main drive gear, receiving rotational torque therefrom, and imparting rotational torque to the respective drive shaft.

Other aspects, features, advantages, etc. will become apparent to one skilled in the art when the description of the preferred embodiments of the invention herein is taken in conjunction with the accompanying drawings.

BRIEF DESCRIPTION OF THE DRAWINGS

For the purposes of illustrating the various aspects of the invention, there are shown in the drawings forms that are presently preferred, it being understood, however, that the invention is not limited to the precise arrangements and instrumentalities shown.

FIGS. 13A and 13B are side and top views, respectively, of a tool for inserting an intervertebral prosthetic device in accordance with one or more further aspects of the present invention;

FIG. 16 is a sectional view of the tool of FIG. 13A, taken through line 16-16;

FIG. 17 is an enlargement of a distal end of the sectional view of FIG. 16;

FIG. 18 is an enlargement of a proximal end of the sectional view of FIG. 16.

DETAILS OF THE EMBODIMENTS OF THE INVENTION

Figure 1A:
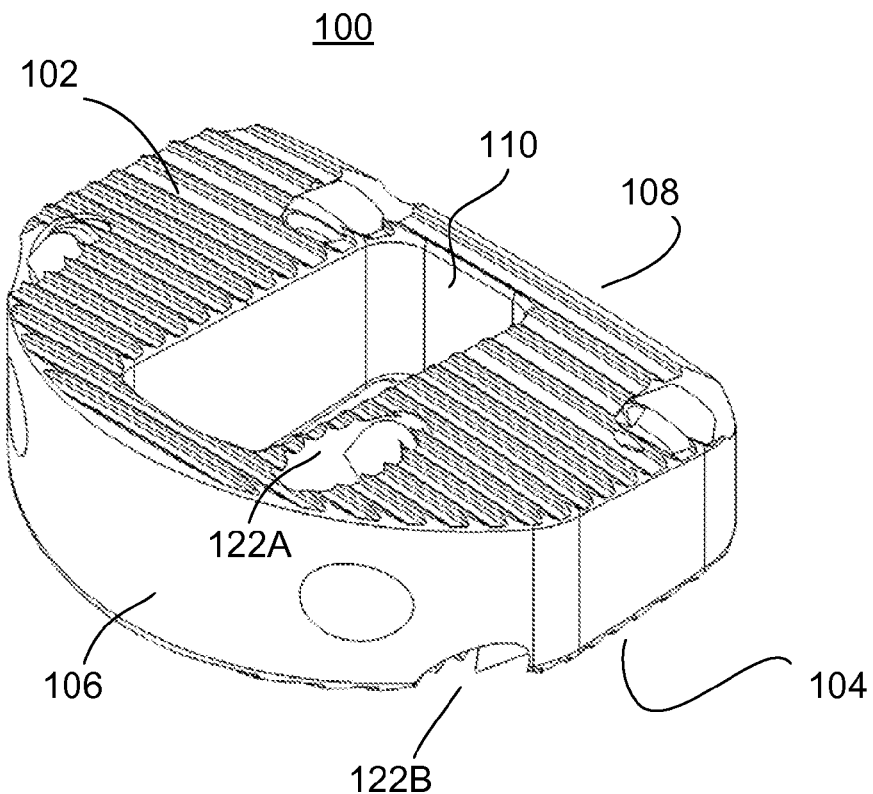
FIG. 1A is a perspective view of an intervertebral prosthetic device in accordance with one or more embodiments of the present invention.
Figure 1B:
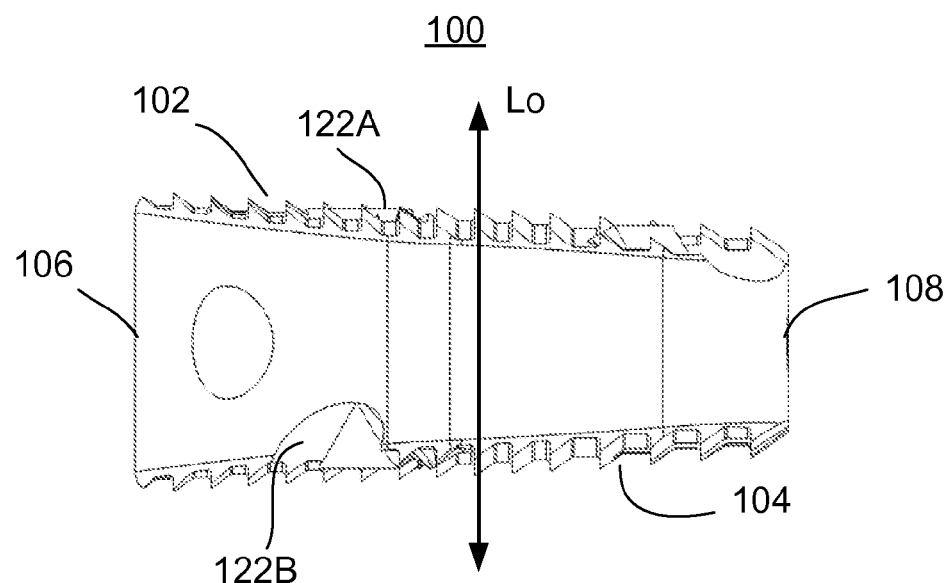
FIG. 1B is a side view of the intervertebral device of FIG. 1.

Reference is now made to FIGS. 1A and 1B, which illustrate an intervertebral prosthetic device 100 in accordance with one or more embodiments of the present invention. FIG. 1A illustrates a perspective view of the intervertebral device 100, while FIG. 1B is a lateral (side) view with the left of the drawing being in the front (anterior) direction and the right of the drawing being in the rear (posterior) direction. The body of the device may be made from any bio-compatible material, such as polyetheretherketone (PEEK), titanium, ceramic, etc.

Figure 2A:
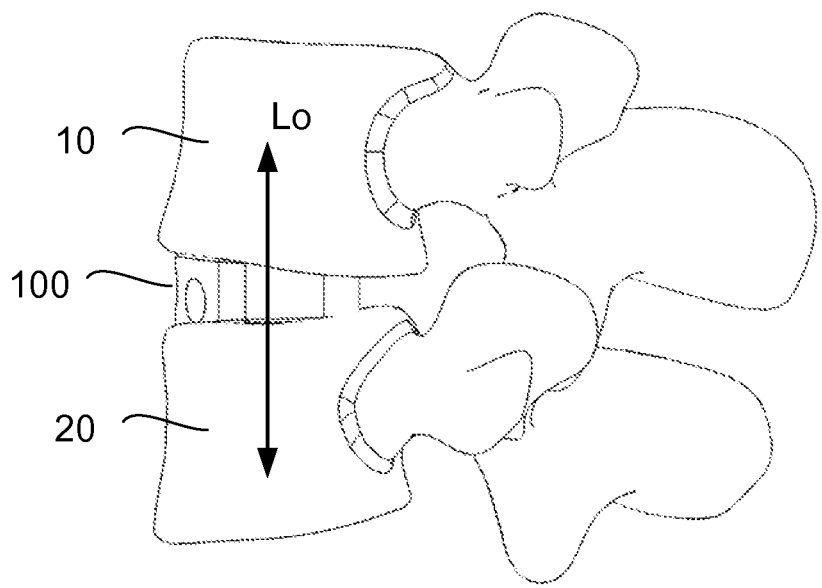
FIGS. 2A-2B are illustrations of the intervertebral device of FIG. 1 in use.

With further reference to FIG. 2A, which shows the device 100 in use, the device 100 generally includes a body (or housing) that is sized and shaped to fit in the intervertebral space between adjacent vertebral bones 10, 20 of the human spine. It is understood that the size and shape of the device 100 may be adapted to fit in an intervertebral space at any level of the spine, such as the cervical spine, thoracic spine, or lumbar spine. The intervertebral device 100 as illustrated in this example is designed to be a stand-alone device (e.g., requiring no separate anchoring devices), which is inserted into the inter-vertebral space from an anterior direction. This embodiment is in the general form of an ALIF device, although as will be appreciated from the description herein, the device may be adapted to operate as a TLIF device, extreme lateral or direct lateral interbody device, PLIF device, or a cervical interbody device.

The body includes first and second spaced apart major surfaces 102, 104 and anterior and posterior sidewalls 106, 108 extending therebetween. The first major surface 102 operates to engage an endplate of the first vertebral bone 10 of the spine, and the second major surface 104 operates to engage an endplate of the adjacent, second vertebral bone 20 of the spine. As best seen in FIGS. 1B and 2A, the first and second major surfaces 102, 104 define a longitudinal axis Lo extending substantially normal to said surfaces and either coaxial with, or generally parallel to, the longitudinal direction of the spine. With reference to FIG. 1B, it is understood that the longitudinal axis Lo is not precisely normal to the first and second major surfaces 102, 104 as there is a slight narrowing height (taper) to the body from the anterior sidewall 106 to the posterior sidewall 108. This taper is designed to accommodate the natural anatomic relationships between the adjacent vertebral bones 10, 20, thereby maintaining the normal lordodic curvature of the spine.

The surgery involved with implanting the device 100 involves removal of the disc material from the intervertebral space, release of the contracted soft tissues around the disc space, and some degree of distraction or pulling apart of the adjacent vertebrae 10, 20 in an attempt to restore disc space height, realign the spine, and indirectly decompress the nerve roots exiting the spine posteriorly at the particular level. After the surgeon removes the disc material, a clean aperture (space) is achieved in which to place the device 100. The surgeon may use a tool to simultaneously grasp the body of the device 100, place it at the mouth of the intervertebral space, and apply force so that the device 100 achieves its final placement.

In order to facilitate desirable adhesion between the endplates of the respective vertebral bones 10, 20 and the device 100, one or both of the first and second major surfaces 102, 104 of the body include a bone engagement feature, such as at least one of serrations, protrusions, valleys, spikes, knurling, keels, etc. Additionally or alternatively, the intervertebral prosthesis 100 may include one or more apertures 110 extending between and through at least one of the first and second major surfaces 102, 104 of the body that operate to permit osteo-inductive growth between the body of the prosthesis 100 and the one or more vertebral bones 10, 20.

Figure 2B:
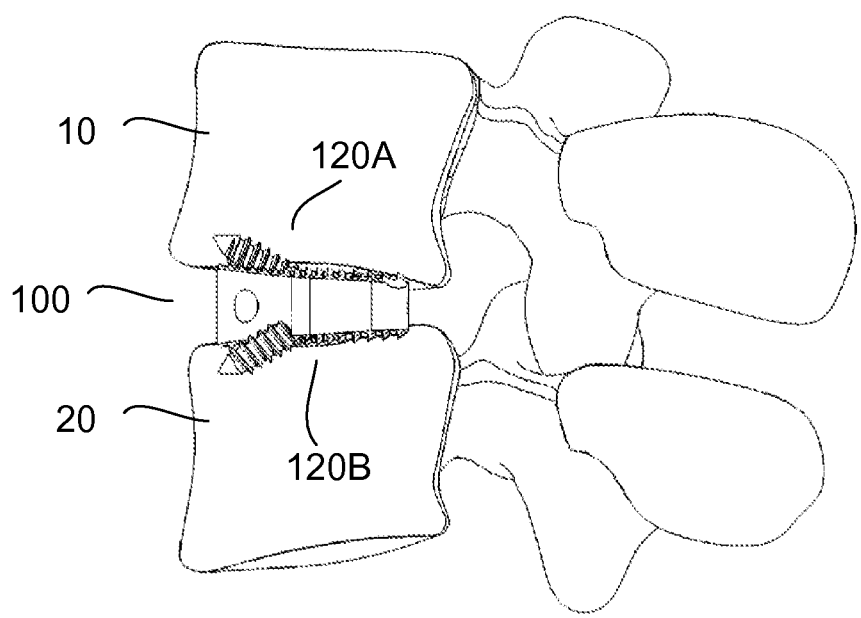

As illustrated in FIG. 2B, once the surgeon has manipulated the device 100 into its proper orientation within the intervertebral space, one or more anchoring elements 120A, 120B, such as threaded screws, are deployed from within the body and engage one or more of the vertebral bones 10, 20. As will be described in more detail herein, the anchoring elements 120A, 120B deploy from the body and thread into the vertebral bones 10, in directions transverse to the longitudinal axis Lo of the body and the spine.

Figure 3A:
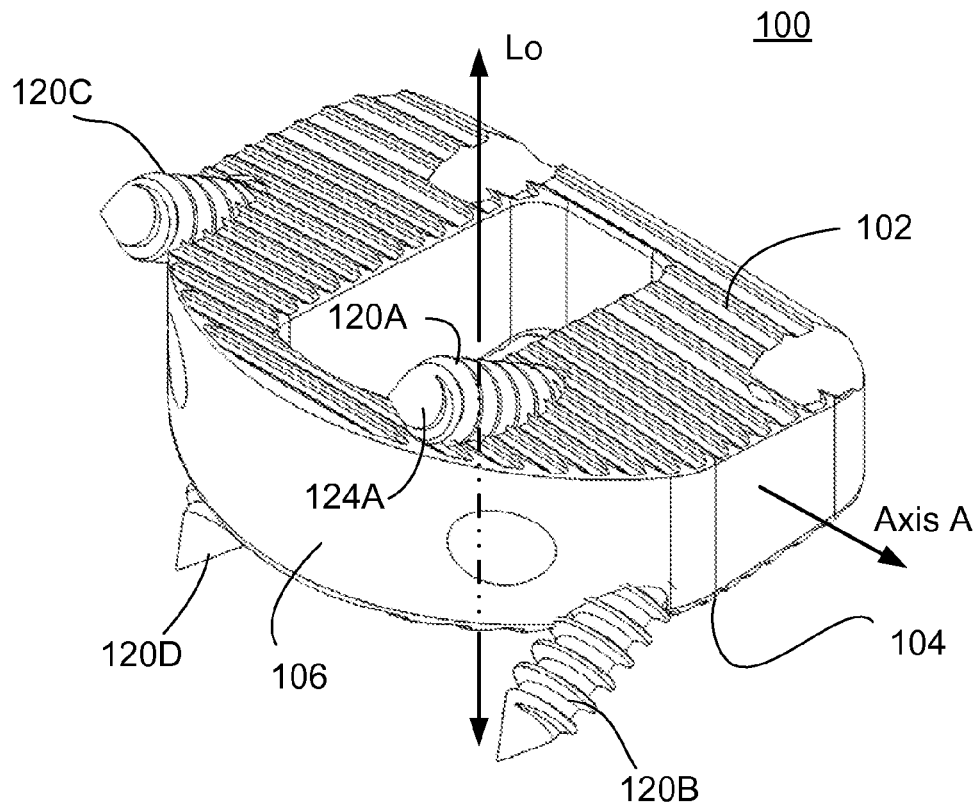
FIG. 3A is a perspective view of the intervertebral prosthetic device with anchoring elements deployed.
Figure 3B:
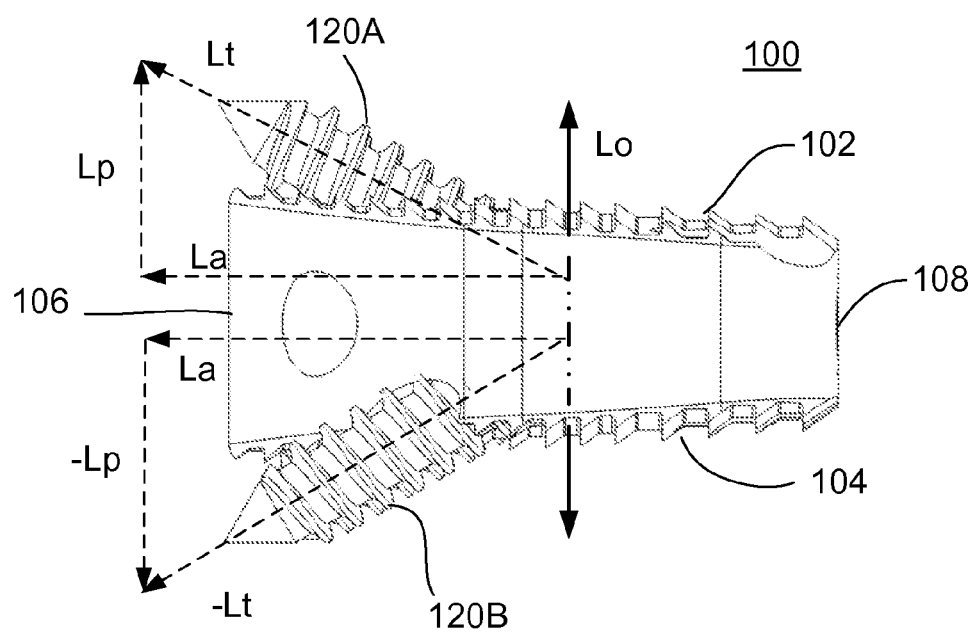
FIG. 3B is a side view of the intervertebral device of FIG. 3.

With reference to FIGS. 1A, 3A, and 3B, the body of the device includes at least a first aperture 122A extending from within the body, transversely with respect to the longitudinal axis Lo, and opening at the first major surface 102. A first anchoring element 120A is disposed within the first aperture 122A in a manner in which deployment of the anchoring element 120A results in a trajectory out of the body and into the given vertebral bone in a direction transverse to the longitudinal axis Lo of the body and the spine. Preferably, the anchoring element 120A is in the form of a threaded shaft having a proximal end and a distal end 124A. Preferably, the distal end 124A and the threads of the first anchoring element 120A are of a self-drilling and self-tapping construction.

The first aperture 122A may be characterized by smooth walls that permit the anchoring element 120A to rotate and translate therethrough during deployment. Alternatively, the first aperture 122A may be characterized by a thread, which matches that of the threaded shaft of the first anchoring element 120A. When the wall of the first aperture 122A is threaded, the rotation of the first anchoring element 120A causes the threads thereof to advance the first anchoring element 120A into the vertebral bone during deployment.

With reference to FIG. 3B, the trajectory Lt of the anchoring element 120A is of importance to achieving desirable fixation of the device 100 within the intervertebral space and avoidance of later migration during use. In this regard, the direction of the first aperture 122A, and thus the direction Lt of deployment of the anchoring element 120A therefrom, is transverse to the longitudinal axis Lo of the body. More particularly, the deployment direction Lt includes a first substantial directional component La in an anterior direction of the body (toward the anterior sidewall 106). The deployment direction Lt also includes a second substantial directional component Lp parallel to the longitudinal axis Lo of the spine. These components of trajectory, Lt=La+Lp, in the anterior and longitudinal directions characterize a significant difference with prior art techniques, where the deployment is fully in the longitudinal direction of the spine.

Although various embodiments of the invention may include a single anchoring element, it is preferred that the device 100 include a plurality of anchoring elements 120, such as including at least a second anchoring element 120B. In this regard, the body of the device 100 may include at least a second aperture 122B extending from within the body, transversely with respect to the longitudinal axis Lo, and opening at the second major surface 104. The second anchoring element 120B may be disposed within the second aperture 122B in a manner in which deployment of the anchoring element 120B results in a trajectory into the given vertebral bone 20 in a direction −Lt transverse to the longitudinal axis Lo of the body and the spine. Preferably, the anchoring element 120A is in the form of a threaded shaft having a proximal end and a distal end 124A. The structural characteristics of the second anchoring element 120B and the second aperture 122B include the options previously discussed with respect to the first anchoring element 120A and first aperture 122A.

Again, the trajectory −Lt of the anchoring element 120B is of importance to achieving desirable fixation of the device 100 within the intervertebral space. The direction of the second anchoring element 120B transverse to the longitudinal axis Lo of the body includes a first substantial directional component La in the anterior direction of the spine, and a second substantial directional component −Lp parallel to the longitudinal axis Lo of the spine, but opposite to the second substantial directional component Lp of the first anchoring element 120A. The transverse and opposite trajectories of the first and second anchoring elements 120A, 120B provide significant improvement in anchoring strength (e.g., improved resistance to sheer stress) as compared with prior art devices.

The anchoring characteristics of the device 100 within the intervertebral space may be adjusted by adding or removing any number of individual anchoring elements 120. In one or more embodiments, such as the device 100 of FIGS. 1A-3B, a first pair of anchoring elements 120A, 120B may be disposed at one lateral side of the body, and a second pair of anchoring elements 120C, 120D (of similar construction) may be disposed at another opposite lateral side of the body. In this embodiment, each of the anchoring elements 120 exhibits a deployment trajectory having a substantial component +/−La in the anterior direction.

Figure 4:
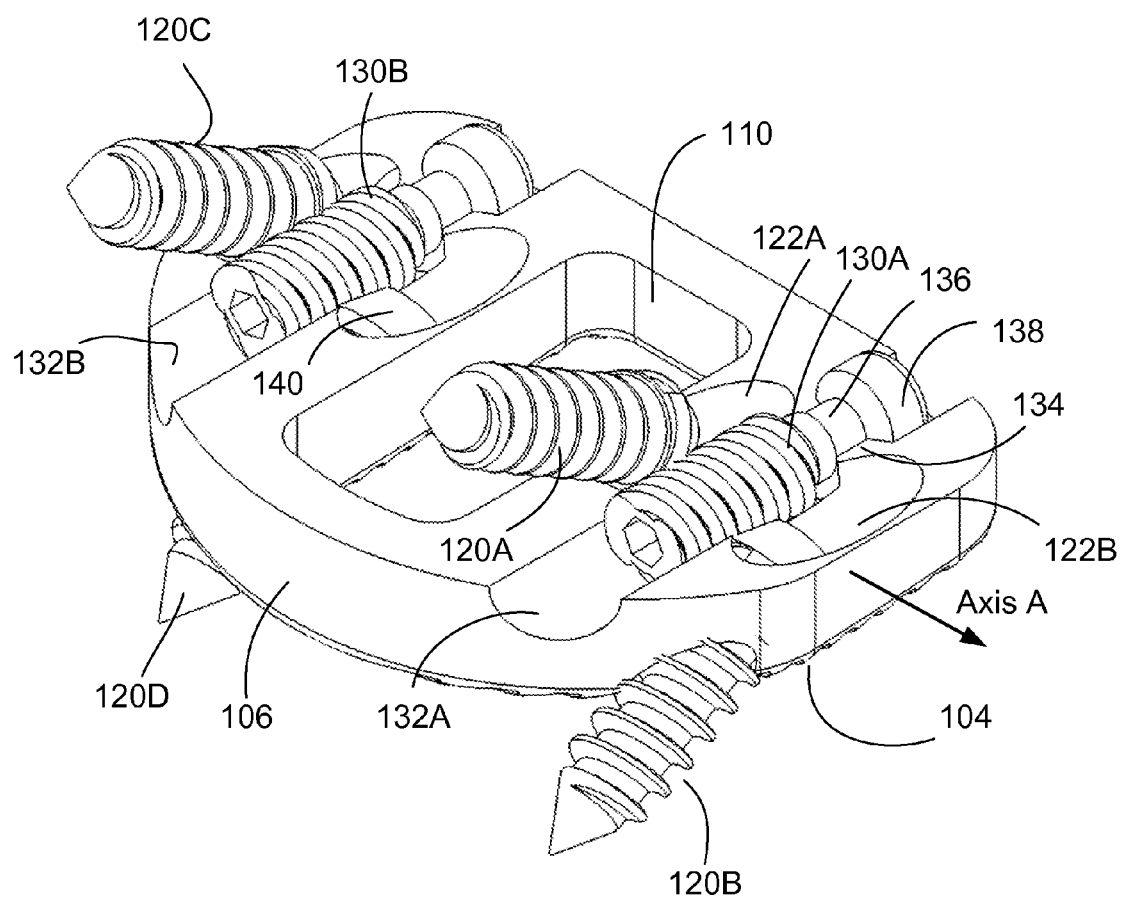
FIG. 4 is a cut-away perspective view of the intervertebral prosthetic device of FIG. 3A showing an example of the inner construction of the device.

Reference is now made to FIG. 4, which illustrates one example of how to implement the deploying anchoring element(s) 120 of the device 100. In particular, the device 100 may include a first gear 130A disposed within a first gear aperture 132A. The first gear 130A is disposed adjacent to, and in meshed, threaded communication with, the threaded shaft of the first anchoring element 120A. The first gear aperture 132A and the first aperture 122A for the first anchoring element 120A are located and oriented such that the apertures intersect over at least a portion thereof, and such that the first anchoring element 120A and the first gear 130A are in meshed, threaded communication at the intersection.

In the illustrated example, the first gear 130A is in the form of a worm gear having a longitudinal orientation in an anterior-posterior direction within the first gear aperture 132A. In this embodiment, the longitudinal orientation of the first gear 130A may be substantially parallel to the first and second major surfaces 102, 104 of the body. Those skilled in the art will appreciate that the threads of the first gear 130A and the threads of the first anchoring element 120A may be readily sized and shaped (in terms of pitch, depth, profile, etc.) such that rotation of the first gear 130A causes rotation of the first anchoring element 120A.

Although various embodiments of the invention may include one anchoring element in communication with the first gear 130A, it is preferred that at least two anchoring elements are in communication with the first gear 130A. Thus, the first gear aperture 132A is located and oriented such that the first gear 130A is also disposed adjacent to, and in meshed, threaded communication with, the threaded shaft of the second anchoring element 120B. The first gear aperture 132A intersects, over at least portions thereof, with each of the first and second apertures 122A, 122B such that the first gear 130A is in meshed, threaded communication at the intersection with each of the first and second anchoring elements 120A, 120B. As best seen in FIG. 4, the intersection of the first gear aperture 130A, the first aperture 122A, and the second aperture 122B, defines an axis A that is oriented laterally with respect to the anterior-posterior direction and parallel to the first and second major surfaces 102, 104 of the body. Those skilled in the art will appreciate that known design techniques may be employed to assure that rotation of the first gear 130A causes rotation of each of the first and second anchoring elements 120A, 120B given the above-described constructional relationships.

The first gear aperture 132A extends toward and opens at at least one of the anterior and posterior sidewalls (in this case the anterior sidewall 106). The first gear 130A includes first and second ends, the first of which is directed toward the aperture opening at the anterior sidewall 106. The first end of the first gear 130A includes a drive tool engagement feature that permits a drive rotational force to be applied to the first gear 130A. (It is noted that the drive tool engagement feature may alternatively or additionally be disposed on the second end of the first gear 130A.) The drive tool engagement feature is illustrated as a hex recess, but may include any of the known or hereinafter developed technologies, such as a star recess, a slot, a Philips head recess, etc. The drive tool (not shown) may access and engage the first gear 130A through the aperture opening at the anterior sidewall 106. The aperture 132A (possibly in combination with another aperture 132B) may also serve as engagement features for an insertion tool used by the surgeon to implant the device within the intervertebral space.

The first gear 130A and the first gear aperture 132A may include a retention feature disposed at the opposing second end of the first gear 130A. The retention feature permits the first gear 130A to rotate but prevents the first gear 130A from moving longitudinally (translating) through the first gear aperture 132A during deployment of the first anchoring element 120A. By way of example, the retention feature includes a throat 134 within the first gear aperture 132A and a corresponding neck 136 and head 138 at the opposite end of the first gear 130A. The throat 134, neck 136 and head 138 cooperate to prevent the first gear 130A from moving longitudinally through the first gear aperture 132A.

As best seen on the exposed portion of the anchoring element 120D of FIG. 4, the anchoring elements may each include a stop member 140, for example, in the form of a head, at a proximal end thereof. With appropriate multiplicities of diameters of the wall of the aperture for the anchor 120D, the stop member 140 may permit the anchor 120D to slide through the associated aperture during deployment but prevent the anchor 120D from exiting the body altogether.

A second gear 130B and associated aperture 132B (of similar construction to that already described) may be disposed on the opposite lateral side of the body to deploy the other anchors 120C, 120D.

Once the anchor elements 120 have been deployed, the one or more gears may be fixed in position by way of the gearing itself, which preferably will not permit the anchor elements 120 to back out of their deployed state. Alternatively, a set screw or any of the other known or hereinafter developed techniques may be used to fix the gearing in place.

Figure 5A:
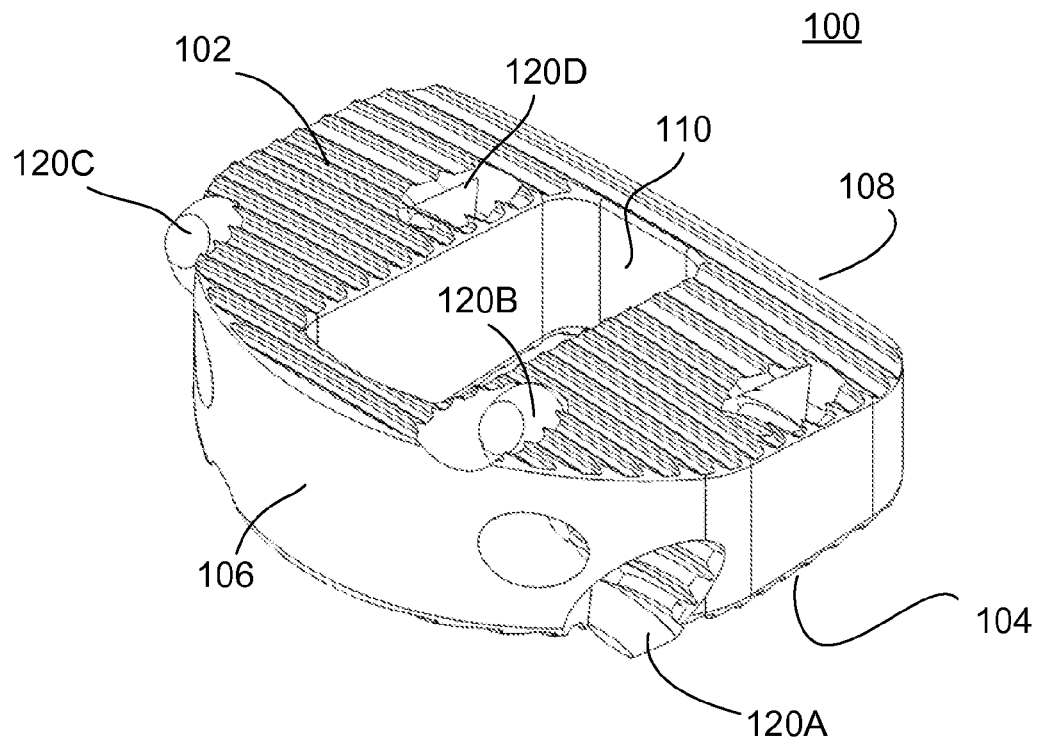
FIG. 5A is a perspective view of an intervertebral prosthetic device in accordance with one or more alternative embodiments of the present invention.
Figure 5B:
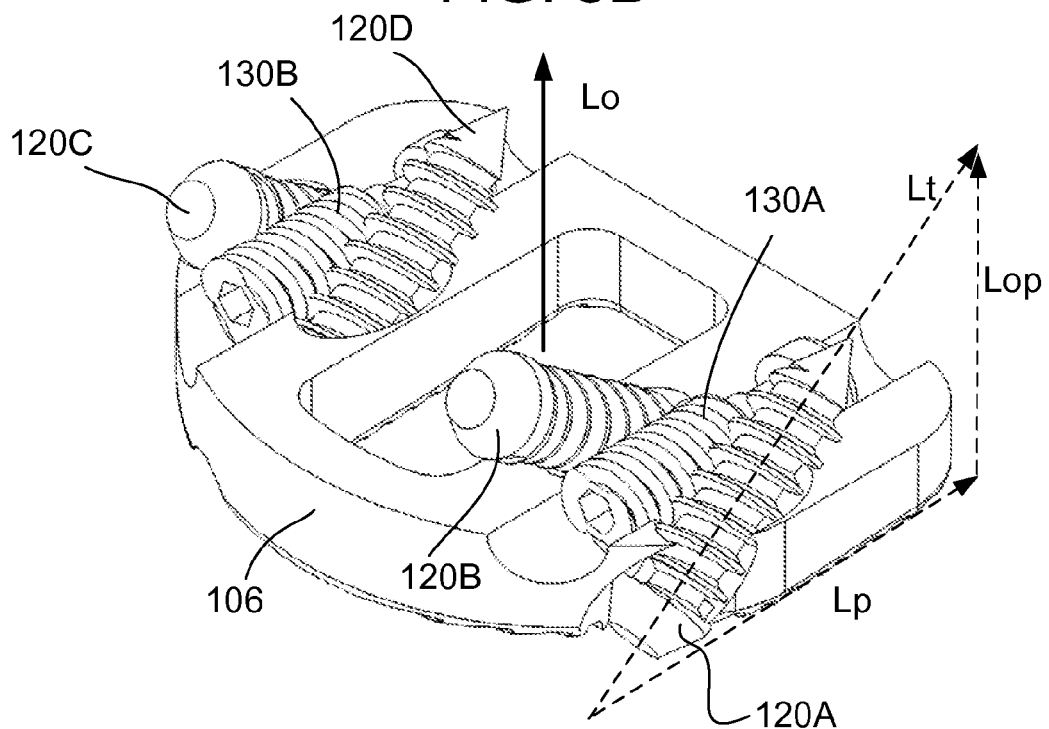
FIG. 5B is a cut-away perspective view of the intervertebral prosthetic device of FIG. 5A showing an example of the inner construction of the device.
Figure 6:
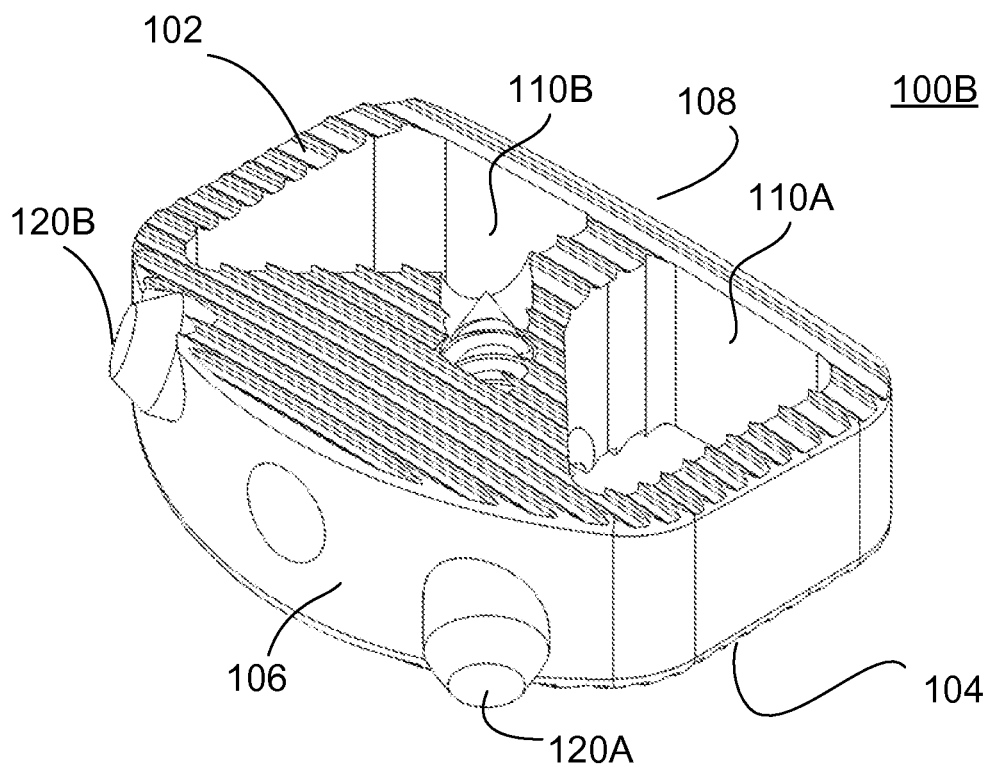
FIG. 6 is a perspective view of an intervertebral prosthetic device in accordance with one or more alternative embodiments of the present invention.
Figure 7:
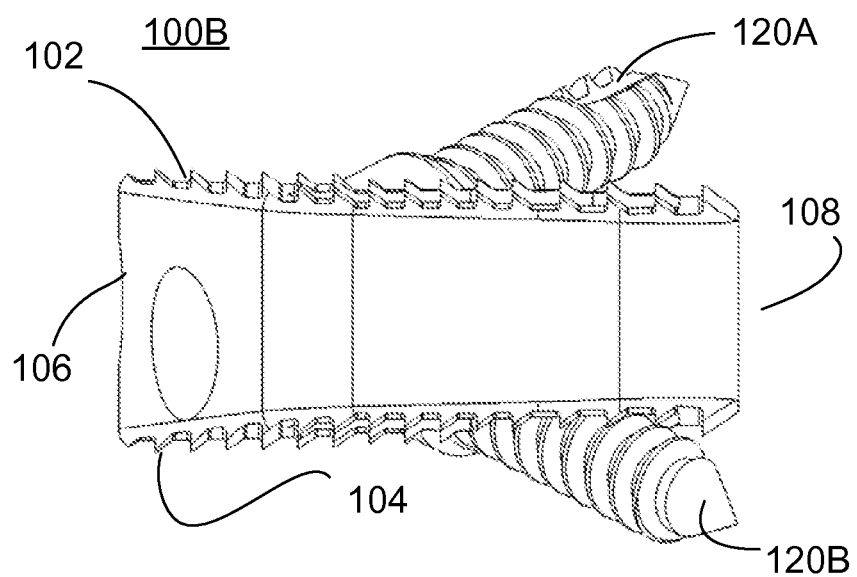
FIG. 7 is a side view of the intervertebral device of FIG. 6.

Reference is now made to FIGS. 5A and 5B, which illustrate an alternative embodiment of an intervertebral prosthesis 100A of the present invention. Those skilled in the art will recognize similarities in the construction of the device 100A with respect to the device 100 described earlier herein. The body of the device 100B includes first and second spaced apart major surfaces 102, 104 and anterior and posterior sidewalls 106, 108 extending therebetween. The first major surface 102 operates to engage an endplate of the first vertebral bone 10 of the spine, and the second major surface 104 operates to engage an endplate of the adjacent, second vertebral bone 20 of the spine. As in other embodiments described herein, one or more anchoring elements 120A, 120B, 120C, 120D may be deployed from within the body and engage one or more of the vertebral bones 10, 20.

With reference to FIG. 5B, the trajectory Lt of the anchoring elements, such as anchoring element 120A is transverse to the longitudinal axis Lo of the body. More particularly, the deployment direction Lt includes a first substantial directional component Lp in a posterior direction of the body (toward the posterior sidewall 108). The deployment direction Lt also includes a second substantial directional component Lop parallel to the longitudinal axis Lo of the spine. The trajectory –Lt (although not shown in the drawing) of the second anchoring element 120B is also transverse to the longitudinal axis Lo of the body. That trajectory includes a first substantial directional component Lp in the posterior direction of the spine, and a second substantial directional component –Lop parallel to the longitudinal axis Lo of the spine, but opposite to the second substantial directional component Lop of the direction of the first anchoring element 120A. The transverse and opposite trajectories of the first and second anchoring elements 120A, 120B provide significant anchoring strength.

Those skilled in the art will appreciate that known design techniques may be employed to assure that rotation of the gears 130A, 130B causes rotation of each of the first and second anchoring elements 120A, 120B, and the third and fourth anchoring elements 120C, 120D, respectively, given the above-described constructional relationships.

Reference is now made to FIGS. 6-9, which illustrate an alternative embodiment of an intervertebral prosthesis 100B of the present invention. Those skilled in the art will again recognize similarities in the construction of the device 100B with respect to the devices 100, 100A described earlier herein. In this embodiment, at least one and preferably a pair of anchoring elements 120A, 120B may be deployed at compound trajectories from within the body and engage one or more of the vertebral bones 10, 20. Given the trajectories of the anchoring elements 120A, 120B, a pair of apertures 110A, 110B extend between and through at least one of the first and second major surfaces 102, 104 of the body and operate to permit osteo-inductive growth between the body of the prosthesis 100B and the one or more vertebral bones 10, 20.

Figure 8:
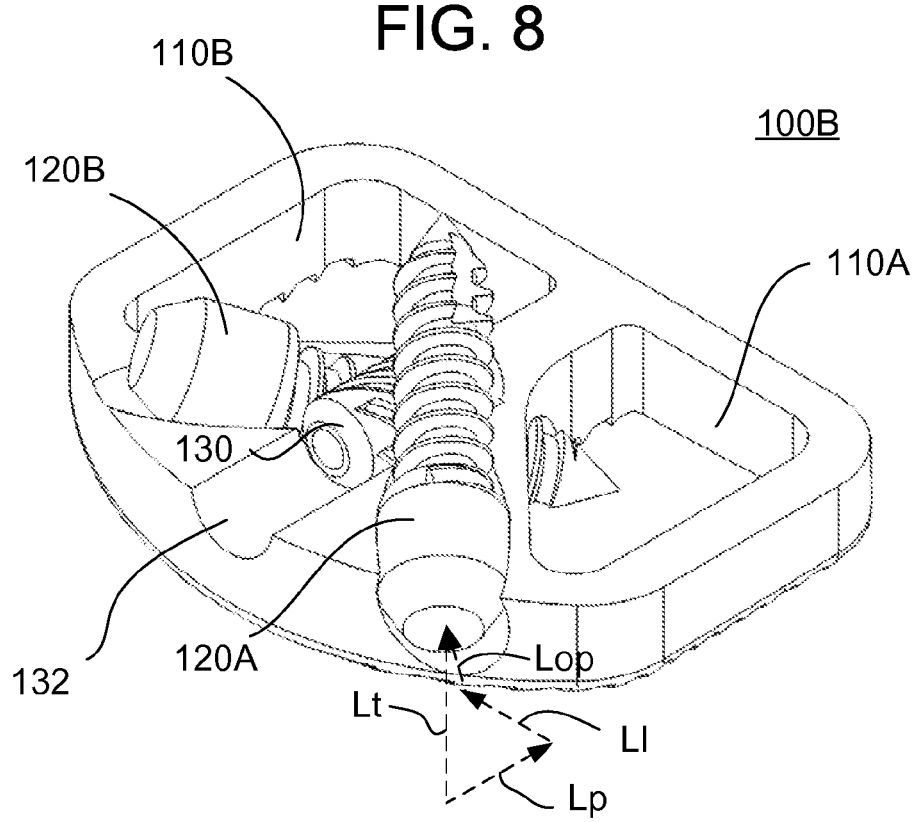
FIG. 8 is a cut-away perspective view of the intervertebral prosthetic device of FIG. 6 showing an example of the inner construction of the device.

With reference to FIG. 8, the trajectory Lt of the anchoring elements, such as anchoring element 120A, is transverse to the longitudinal axis Lo of the body. More particularly, the deployment direction Lt includes a first substantial directional component Lp in a posterior direction of the body (toward the posterior sidewall 108), a second substantial directional component Lop parallel to the longitudinal axis Lo of the spine, and a third substantial directional component Ll in a lateral direction with respect to the anterior-posterior direction of the spine. The trajectory –Lt of the second anchoring element 120B is also transverse to the longitudinal axis Lo of the body. That trajectory includes a first substantial directional component Lp in the posterior direction of the spine, a second substantial directional component –Lop parallel to the longitudinal axis Lo of the spine, but opposite to the second substantial directional component Lop of the first anchoring element 120A, and a third substantial directional component –Ll in a lateral direction with respect to the anterior-posterior direction of the spine and opposite to the third substantial directional component Ll of the first anchoring element 120A. These compound transverse and opposite trajectories of the first and second anchoring elements 120A, 120B provide significant anchoring strength.

Figure 9:
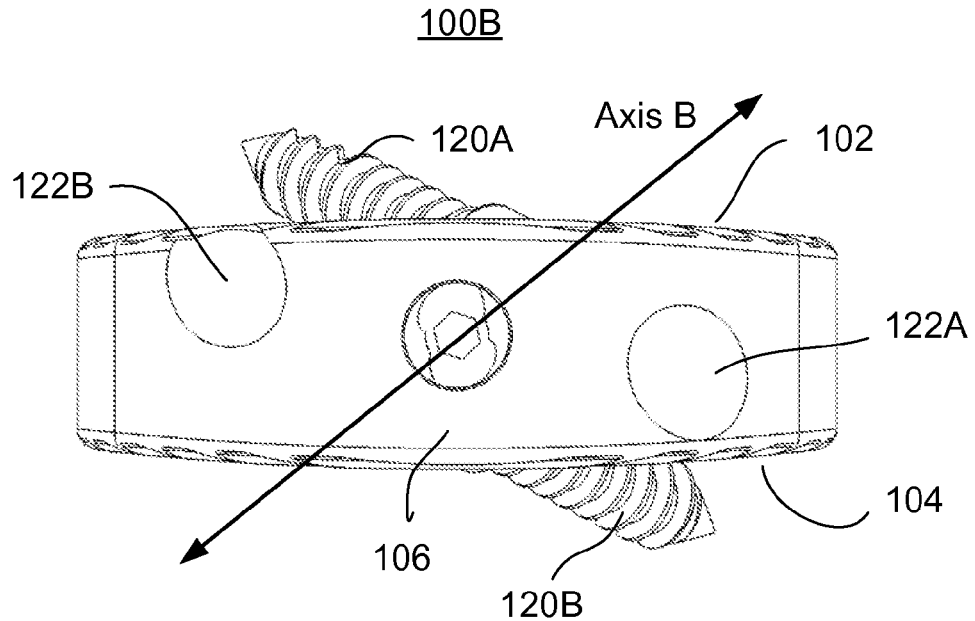
FIG. 9 is a front view of the intervertebral device of FIG. 6.

With reference to FIGS. 8-9, an example is illustrated as to how to implement the deploying anchoring elements 120A, 120B of the device 100B. In particular, the device 100B may include a gear 130 disposed within a gear aperture 132, where the gear 130 is disposed adjacent to, and in meshed, threaded communication with, the threaded shafts of the first and second anchoring elements 120A, 120B. The gear aperture 132, the first aperture 122A for the first anchoring element 120A, and the second aperture 122B for the second anchoring element 120B are located and oriented such that the apertures intersect over at least a portion thereof. As best seen in FIG. 9, the intersection of the gear aperture 130, the first aperture 122A, and the second aperture 122B, defines an axis B that is oriented transverse to the longitudinal axis of the body, transverse to the anterior-posterior direction of the body, and transverse to the first and second major surfaces 102, 104 of the body. The gear 130 and the first and second anchoring elements 120A, 120B are in meshed, threaded communication at and along the direction (axis B) of the intersection.

In the illustrated example, the gear 130 is in the form of a helical gear having a longitudinal orientation in an anterior-posterior direction within the gear aperture 132. In this embodiment, the longitudinal orientation of the gear 130 may be substantially parallel to the first and second major surfaces 102, 104 of the body. Those skilled in the art will appreciate that the threads of the gear 130 and the threads of the first and second anchoring elements 120A, 120B may be readily sized and shaped (in terms of pitch, depth, profile, etc.) such that rotation of the gear 130 causes rotation of the first and second anchoring elements 120A, 120B in the proper rotational directions to thread the anchoring elements into the vertebral bones 10, 20.

Those skilled in the art will recognize that variations in the design of the device 100B are possible. For example, given the disclosure herein, one skilled in the art will appreciate that the trajectories of the first and second anchoring elements 120A, 120B may be reversed (at least in the anterior-posterior direction), such that the deployment direction Lt of the first anchoring element 120A includes a first substantial directional component La in an anterior direction of the body (toward the anterior sidewall 106), a second substantial directional component Lp parallel to the longitudinal axis Lo of the spine, and a third substantial directional component Ll in a lateral direction with respect to the anterior-posterior direction of the spine. The trajectory –Lt of the second anchoring element 120B may include a first substantial directional component La in the anterior direction of the spine, a second substantial directional component –Lp parallel to the longitudinal axis Lo of the spine, but opposite to the second substantial directional component Lp of the first anchoring element 120A, and a third substantial directional component –Ll in a lateral direction with respect to the anterior-posterior direction of the spine and opposite to the third substantial directional component Ll of the first anchoring element 120A.

Figure 10:
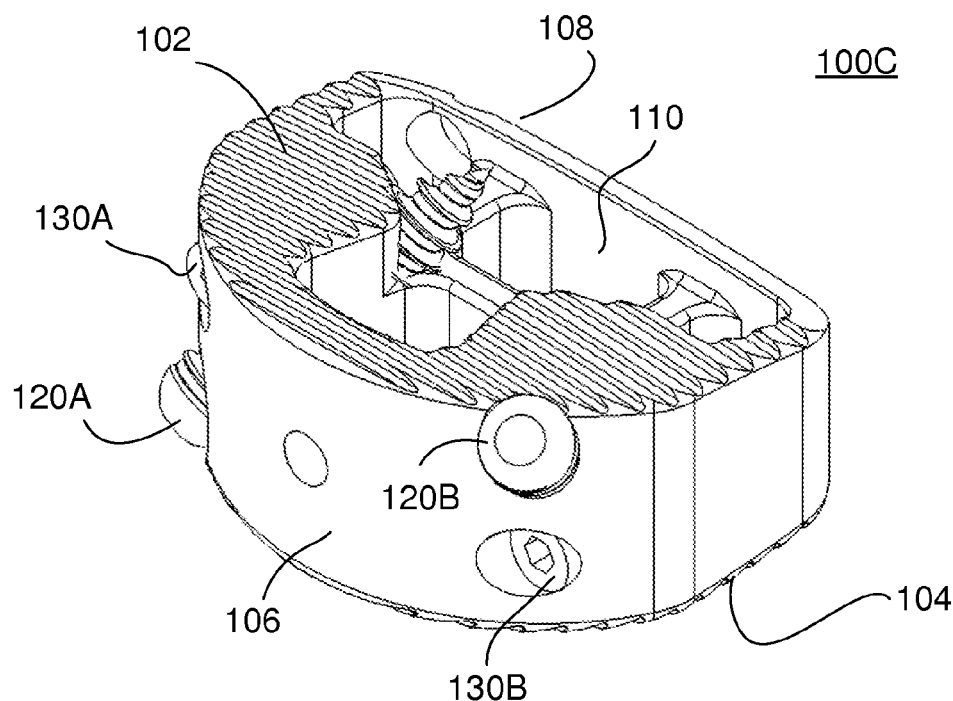
FIG. 10 is a perspective view of an intervertebral prosthetic device in accordance with one or more alternative embodiments of the present invention.
Figure 11:
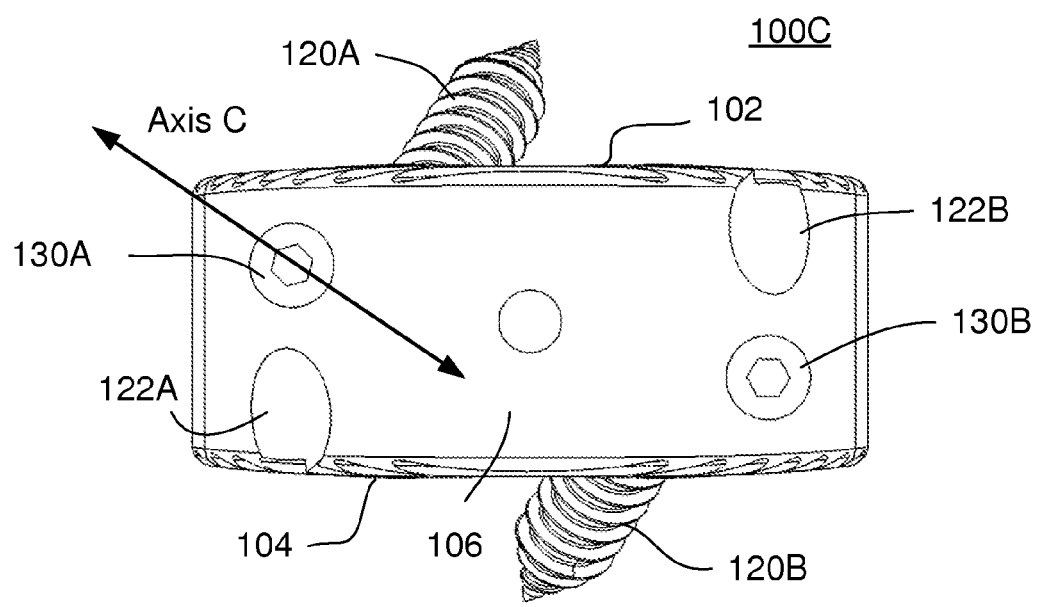
FIG. 11 is a front view of the intervertebral device of FIG. 10.
Figure 12:
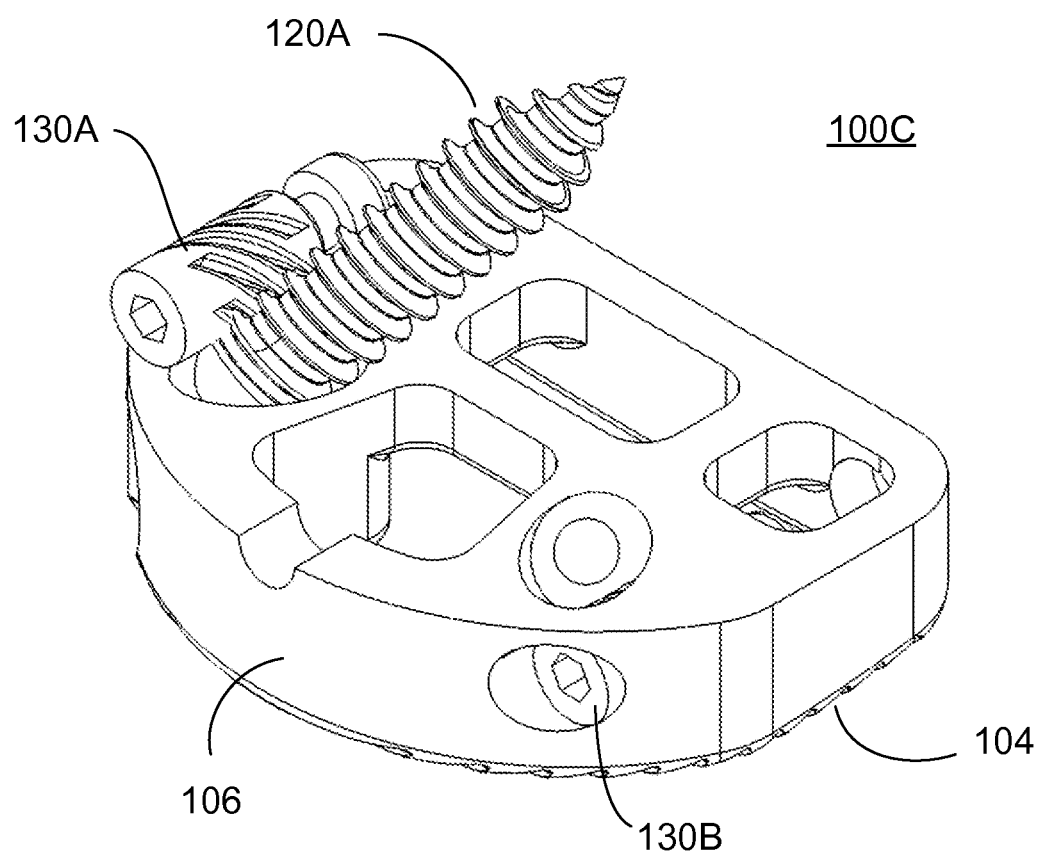
FIG. 12 is a cut-away perspective view of the intervertebral prosthetic device of FIG. 10 showing an example of the inner construction of the device.

Reference is now made to FIGS. 10-12, which illustrate an alternative embodiment of an intervertebral prosthesis 100C of the present invention. Those skilled in the art will again recognize similarities in the construction of the device 100C with respect to the devices 100, 100A, and 100B described above. In this embodiment, at least one and preferably a pair of anchoring elements 120A, 120B may be deployed at compound trajectories from within the body and engage one or more of the vertebral bones 10, 20. In contrast to the device 100B, however, this embodiment includes separate driving gears to deploy each of the anchoring elements 120A, 120B.

The trajectories Lt, –Lt of each of the anchoring elements 102A, 102B of the device 100C may be described in substantially the same way as the trajectories of the device 100B (including the ability, with modification, to be generally directed to the posterior direction as shown, or alternatively in the anterior direction).

With reference to FIG. 12, an example is illustrated as to how to implement the deploying anchoring elements 120A, 120B of the device 100C. In particular, the device 100C may include a first gear 130A disposed within a first gear aperture 132A, where the first gear 130A is disposed adjacent to, and in meshed, threaded communication with, the threaded shaft of the first anchoring element 120A. The first gear aperture 132A and the first aperture 122A for the first anchoring element 120A are located and oriented such that the apertures intersect over at least a portion thereof. As best seen in FIG. 11, the intersection of the first gear aperture 130A and the first aperture 122A defines an axis C that is oriented transverse to the longitudinal axis of the body, transverse to the anterior-posterior direction of the body, and transverse to the first and second major surfaces 102, 104 of the body. The first gear 130A and the first anchoring element 120A are in meshed, threaded communication at and along the direction (axis C) of the intersection.

In the illustrated example, the first gear 130A is in the form of a helical gear having a longitudinal orientation in an anterior-posterior direction within the first gear aperture 132A. In this embodiment, the longitudinal orientation of the first gear 130A may be substantially parallel to the first and second major surfaces 102, 104 of the body. Those skilled in the art will appreciate that the threads of the first gear 130A and the threads of the first anchoring element 120A may be readily sized and shaped (in terms of pitch, depth, profile, etc.) such that rotation of the first gear 130A causes rotation of the first anchoring element 120A in the proper rotational direction to thread the anchoring elements into the vertebral bones 10, 20.

The construction of the second gear 130B, the second anchoring element 120B, and the respective apertures 132B, 122B, therefor, are of substantially similar characteristics, and thus a detailed discussion thereof will not be repeated.

Reference is now made to FIGS. 13-19, which illustrate a tool 200 for assisting the surgeon in implanting the device 100 in the patient's spine. As will be discussed in more detail below, the surgeon may use the tool 200 to simultaneously grasp the body of the device 100, place it at the mouth of the intervertebral space, and apply force so that the device 100 achieves its final placement. Thereafter, an element of the tool 200 is manipulated by the surgeon to cause the one or more anchoring elements 120 to deploy from within the body and engage one or more of the vertebral bones 10, 20 in directions transverse to the longitudinal axis Lo of the body and the spine.

With specific reference to FIGS. 13A and 13B, which are side and top views, respectively, the tool 200 includes a handle 202 disposed at a proximal end, and a chuck 204 disposed at a distal end thereof. As will be developed in more detail below, the chuck 204 is operable to releasably engage the intervertebral stabilizer 100 such that the surgeon may manipulate the position of the stabilizer 100 by way of the handle 202 in order to urge the stabilizer 100 into the intervertebral space.

The handle 202 includes a drive nut 206 operating to produce rotational torque in response to user-input. The rotational torque of the drive nut 206 is transferred to one or more of first and second drive shafts 208, 210, causing the dive shaft(s) to turn and produce rotational torque(s) at the distal end of the tool 200. More specifically, each of the first and second drive shafts 208, 210 includes proximal and distal ends, the proximal ends being in communication with the drive nut 206, receiving rotational torque therefrom, and imparting rotational torques to the respective drive shafts about respective first and second axes A1, A2. The first and second drive shafts 208, 210 extend through, and are rotatable within, the chuck 204. The distal ends of the first and second drive shafts 208, 210 each include a respective drive head 212, 214. Each of the first and second drive heads 212, 214 are sized and shaped to engage a respective one of the first and second gears 130A, 130B of the intervertebral stabilizer 100. By way of example, the first and second drive heads 212, 214 may be of a hexagonal design, a star design, a slot design, a Philips-head design, etc. Thus, rotation of the drive nut 206 results in rotation and deployment of the anchoring elements 120 of the intervertebral prosthesis 100.

Figure 14:
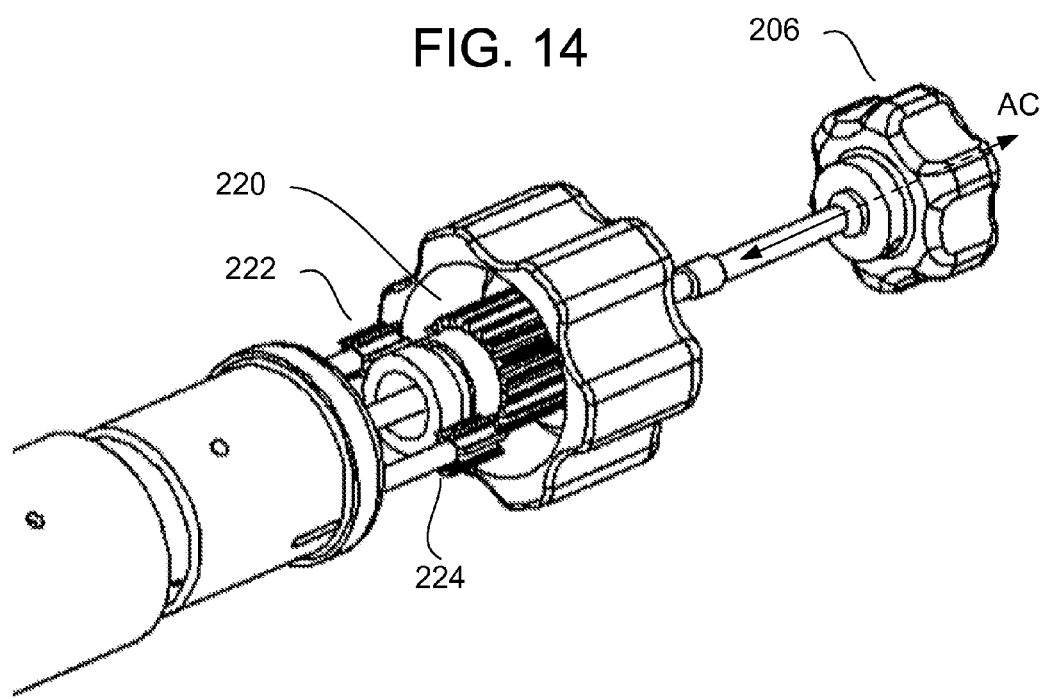
FIG. 14 is an exploded view of a proximal end of the tool of FIGS. 13A and 13B.
Figure 15:
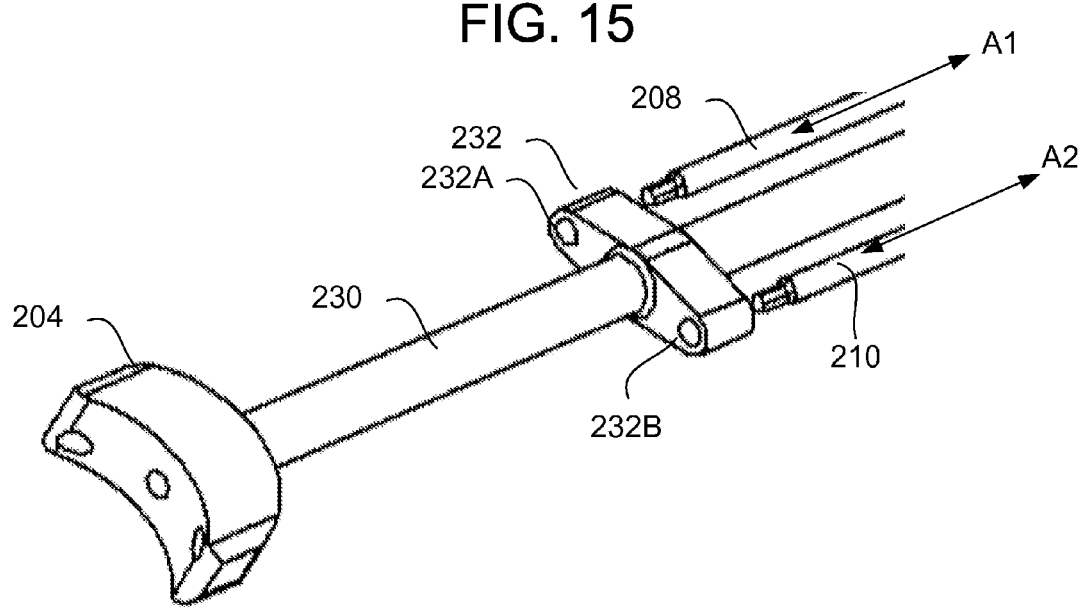
FIG. 15 is an exploded view of a distal end of the tool of FIGS. 13A and 13B.

Reference is now made to FIGS. 14 and 15, which are exploded views of the proximal and distal ends of the tool 200, respectively, in accordance with one or more embodiments. The drive nut 206 operates to produce rotational torque about a central axis, AC, which is laterally offset from each of the first and second axes A1, A2 of the first and second drive shafts 208, 210. The handle 202 further includes a main drive gear 220, which is rotatable about the central axis AC, and is coupled to, and receives the rotational torque from, the drive nut 206. The proximal ends of the first and second drive shafts 208, 210 each include a pickup gear 222, 224 in meshed communication with the main drive gear 220. Thus, each of the first and second pickup gears 222, 224 receive rotational torque from the main drive gear 220, and impart rotational torque to the respective first and second drive shafts 208, 210. By way of example, the main drive gear 220, and the first and second drive gears 222, 224 may be spur gears; however, any other appropriate gear type and orientation are possible, such as helical gears, worm gears, external and/or internal gears, etc.

Reference is now made to FIGS. 16-18, where FIG. 16 is a sectional view of the tool 200 of FIG. 13A, taken through line 16-16, and FIGS. 17-18 are enlargements of the distal and proximal ends of the sectional view, respectively. As best seen in FIG. 16, the tool 200 includes a central housing 230 extending generally from the handle 202 to the chuck 204. The central housing 230 operates to maintain proper orientation as between the handle 202 and the chuck 204 as well as other functions that will be discussed later herein. In addition, the tool 200 may include a bushing section 232 that operates to maintain the respective orientations of the first and second drive shafts 208, 210. By way of example, the first and second drive shafts 208, 210 may be substantially parallel to one another along their lengths. In this regard, and with further reference to FIG. 15, the bushing section 232 may include a pair of apertures 232A, 232B, which permit the first and second drive shafts 208, 210 to slide and rotate therein. As best seen in FIG. 18, the parallel relationship of the first and second drive shafts 208, 210 (and thus the respective axes A1, A2 thereof) are maintained via the structures of the handle 202, the bushing 232, and the chuck 204. In addition the respective axes A1, A2 are both laterally offset from the central axis AC of the drive nut 206.

With specific reference to FIG. 17, the central housing 230 may include a retaining rod 234 extending therethrough and operating to couple the intervertebral prosthesis 100 to the chuck 204 during insertion thereof into the spine. By way of example, the retaining rod 234 may include a proximal end coupled to the handle 202 and a distal end operating to couple to the intervertebral prosthesis 100. The distal end of the retaining rod 234 may include a specific engagement feature 236 that includes structure suitable for connection to the intervertebral prosthesis 100. By way of example, the engagement feature 236 may be threaded and capable of threading into a complementary threaded bore within the intervertebral prosthesis 100. In this regard, the retaining rod 234 may extend through the handle 202 to the drive nut 206, such that the user (e.g., the surgeon) may couple the intervertebral prosthesis 100 to the tool 200 by way of rotating the drive nut 206.

Additionally or alternatively, the retaining rod 234 may operate as a drive shaft to deploy one or more anchors 120 from the intervertebral prosthesis 100. For example, the intervertebral prosthesis 100 may include certain features illustrated in FIGS. 8-9, such as the central gear 130 in meshed, threaded communication with, one or more of the threaded shafts of the first and second anchoring elements 120A, 120B. In such an example, the retaining rod 234 may operate as a central drive shaft, where the proximal end thereof is coupled to the main drive gear 220, receiving rotational torque therefrom, and imparting rotational torque to the central drive shaft about the central axis AC. The distal end of the central drive shaft may include a central drive head, which operates to engage the central gear 130 of the intervertebral prosthesis 100. Thus, rotation of the drive nut 206 causes rotation of the central gear 130 and deployment of one or more of the anchoring elements 120 of the intervertebral prosthesis 100.

Figure 19:
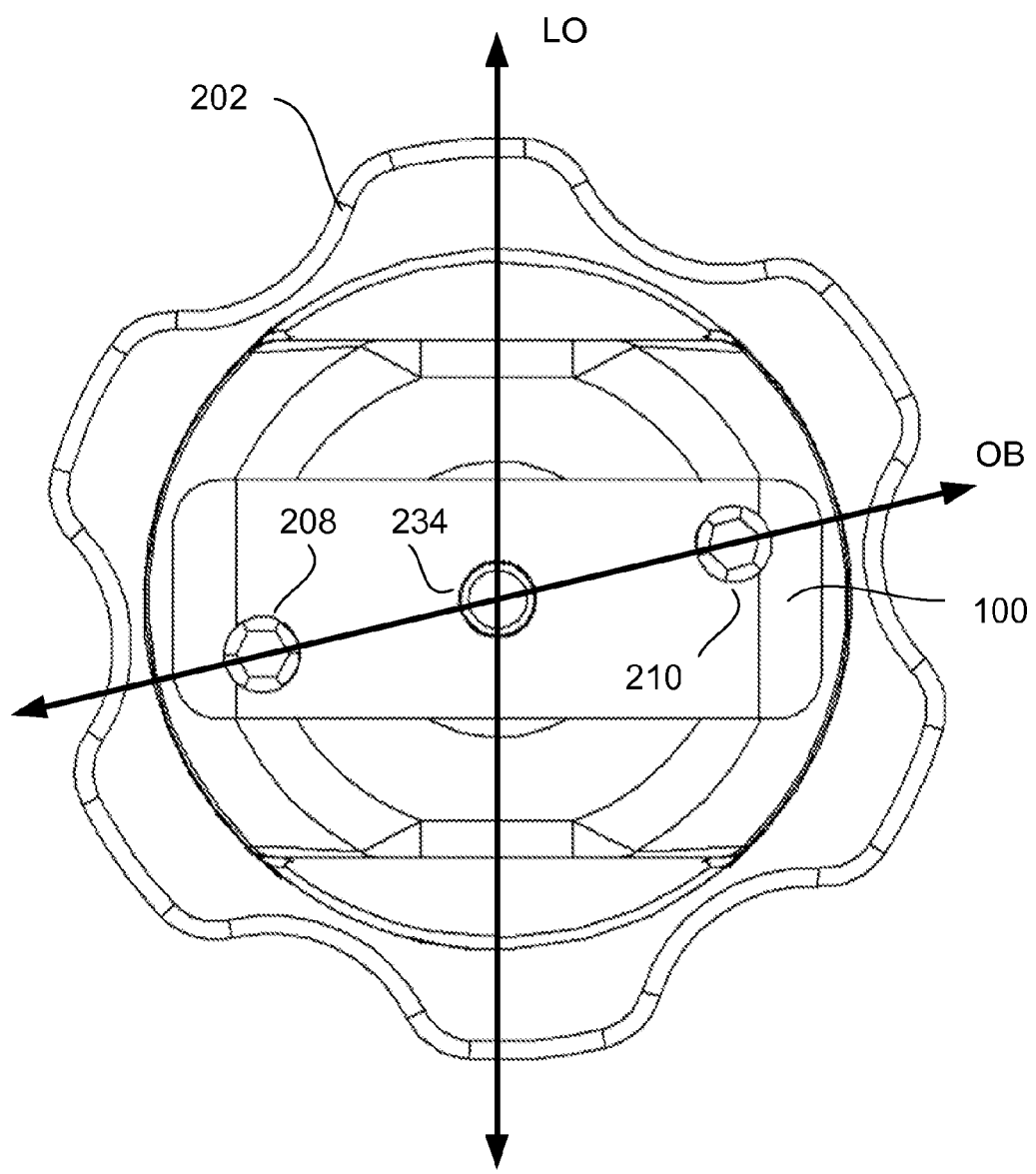
FIG. 19 is an end view of the tool of FIGS. 13A and 13B showing alternative or additional features in accordance with one or more further aspects of the invention.

Reference is now made to FIG. 19, which is an end view of the tool 200 of FIGS. 13A and 13B showing alternative or additional features in accordance with one or more further aspects of the invention. In particular, the first and second drive shafts 208, 210 lay in a plane OB that is oblique to the longitudinal axis LO of the intervertebral prosthesis 100. This is advantageous in that, when two drive shafts are employed (e.g., shafts 208, 210), the shafts may align with offset drive gears 130A, 130B, of the intervertebral prosthesis 100, such as is illustrated in FIGS. 10-12. Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An apparatus for inserting an intervertebral prosthesis within a spine of a mammal, comprising:
   a handle disposed at a proximal end of the tool and including a drive nut operating to produce rotational torque in response to user-input;
   a main drive gear rotatable about a central axis, and coupled to, and receiving the rotational torque from, the drive nut;
   a first drive shaft including proximal and distal ends; the proximal end including a first pickup gear in meshed communication with the main drive gear, receiving rotational torque therefrom, and imparting rotational torque to the first drive shaft about a first axis, which is laterally offset from the central axis; and the distal end of the first drive shaft including a first drive head;
   a chuck disposed at the distal end of the tool and being sized and shaped to engage the intervertebral prosthesis during implantation,
   wherein the first drive shaft extends through the chuck such that the first drive head operates to engage a first gear of the intervertebral prosthesis, such that rotation of the first gear causes rotation and deployment of a first anchoring element of the intervertebral prosthesis.

2. The apparatus of claim 1, further comprising:
   a second drive shaft including proximal and distal ends; the proximal end including a second pickup gear in meshed communication with the main drive gear, receiving rotational torque therefrom, and imparting rotational torque to the second drive shaft about a second axis, which is laterally offset from both the central axis and the first axis; and the distal end of the second drive shaft including a second drive head,
   wherein the second drive head operates to engage a second gear of the intervertebral prosthesis, such that rotation of the second gear causes rotation and deployment of a second anchoring element of the intervertebral prosthesis.

3. The apparatus of claim 2, wherein the first and second drive shafts are substantially parallel to one another.

4. The apparatus of claim 2, wherein the main drive gear and the first and second drive gears are spur gears.

5. The apparatus of claim 2, wherein:
   the first and second drive shafts lay in a plane that is oblique to a longitudinal axis of the intervertebral prosthesis; and
   the intervertebral prosthesis includes a body having first and second spaced apart major surfaces and at least anterior and posterior sidewalls extending therebetween, the first major surface for engaging an endplate of a first vertebral bone of the spine, and the second major surface for engaging an endplate of an adjacent, second vertebral bone of the spine, and the longitudinal axis extends substantially normal to the first and second major surfaces.

6. The apparatus of claim 1, further comprising:
   a central drive shaft including proximal and distal ends;
   the proximal end coupled to the main drive gear, receiving rotational torque therefrom, and imparting rotational torque to the central drive shaft about the central axis; and the distal end of the central drive shaft including a central drive head,
   wherein the central drive head operates to engage a central gear of the intervertebral prosthesis, such that rotation of the central gear causes rotation and deployment of one or more anchoring elements of the intervertebral prosthesis.

7. (The apparatus of claim 1, further comprising a central housing, wherein the handle is connecting to one end thereof and the chuck is connected to an opposite end thereof.

8. The apparatus of claim 7, further comprising a retaining rod extending through the central housing and operating to couple the intervertebral prosthesis to the chuck during insertion thereof into the spine.

9. An apparatus for inserting an intervertebral prosthesis within a spine of a mammal, comprising:
   an insertion tool, comprising: (i) a handle disposed at a proximal end of the tool and including a drive nut operating to produce rotational torque in response to user-input about a central axis; and a first drive shaft including proximal and distal ends; the proximal end in communication with the drive nut, receiving rotational torque therefrom, and imparting rotational torque to the first drive shaft about a first axis, which is laterally offset from the central axis; and the distal end of the first drive shaft including a first drive head,
   a first gear of the intervertebral prosthesis, such that rotation of the first gear causes rotation and deployment of a first anchoring element of the intervertebral prosthesis.

10. The apparatus of claim 9, further comprising a chuck disposed at the distal end of the tool and being sized and shaped to engage the intervertebral prosthesis during implantation, wherein the first drive shaft extends through the chuck such that the first drive head operates to engage the first gear of the intervertebral prosthesis.

11. The apparatus of claim 9, further comprising:
   a second drive shaft including proximal and distal ends; the proximal end being in communication with the drive nut, receiving rotational torque therefrom, and imparting rotational torque to the second drive shaft about a second axis, which is laterally offset from both the central axis and the first axis; and the distal end of the second drive shaft including a second drive head,
   wherein the second drive head operates to engage a second gear of the intervertebral prosthesis, such that rotation of the second gear causes rotation and deployment of a second anchoring element of the intervertebral prosthesis.

* * * * *